United States Patent [19]

Georgi

[11] 4,137,913
[45] Feb. 6, 1979

[54] FLUID FLOW CONTROL SYSTEM

[75] Inventor: Heinz W. Georgi, Del Mar, Calif.

[73] Assignee: IVAC Corporation, San Diego, Calif.

[21] Appl. No.: 554,092

[22] Filed: Feb. 28, 1975

[51] Int. Cl.$^2$ .............................................. A61M 5/14
[52] U.S. Cl. ............................ 128/214 F; 128/214 E; 128/DIG. 12; 128/DIG. 13; 222/63
[58] Field of Search ............... 128/1 D, 214 E, 214 F, 128/218 A, DIG. 12, DIG. 13, DIG. 1; 421/9, 19, 20, 44, 326, 410; 222/63

[56] References Cited

U.S. PATENT DOCUMENTS

| | | | |
|---|---|---|---|
| 3,559,644 | 2/1971 | Stoft et al. | 128/214 F |
| 3,724,720 | 4/1973 | Bullivant | 222/63 |
| 3,731,679 | 5/1973 | Wilhelmson et al. | 128/214 F |
| 3,736,930 | 6/1973 | Georgi | 128/214 E |
| 3,812,482 | 5/1974 | Clark | 128/214 E |
| 3,884,228 | 5/1975 | Hahn | 128/214 F |
| 3,887,110 | 6/1975 | Porter | 222/63 |
| 3,888,239 | 6/1975 | Rubinstein | 128/214 F |
| 3,890,968 | 6/1975 | Pierce et al. | 128/214 E |
| 3,985,133 | 10/1976 | Jenkins et al. | 128/214 F |

Primary Examiner—William E. Kamm
Attorney, Agent, or Firm—Fulwider, Patton, Rieber, Lee & Utecht

[57] ABSTRACT

A syringe pump operated by a stepping motor to repetitively fill and empty a syringe cartridge over a plurality of operational cycles of successive fill stroke and pump stroke periods. The motor is driven by drive pulses from a digital pulse generation and control system, the pulse frequency establishing a predetermined fixed rate of fill during the fill stroke and being preselected, in accordance with desired output flow rate, to establish the rate at which the syringe is emptied during the pump stroke. The drive pulse rate during a fill stroke exceeds the maximum pulse rate during a pump stroke and, in order to maintain a proportional relationship between the preselected pumping rate and the actual pumping rate over each complete cycle of successive fill and pump strokes, the drive pulse frequency during each pump stroke is automatically increased to compensate for the time lost during each fill stroke. This is accomplished by accelerating counting up of the electrical network defining each individual pump stroke drive pulse period for a time interval equal to a single fill stroke drive pulse period. A start-up subsystem insures proper cartridge installation prior to initiation of a pumping cycle. Appropriate alarms respond to improper operating conditions including leakage from the source during the pump stroke, empty bottle or insufficient flow during fill, air in the I.V. line, a stalled motor, lack of flow due to system component failure, or occurrence of a runaway high pumping rate.

59 Claims, 19 Drawing Figures

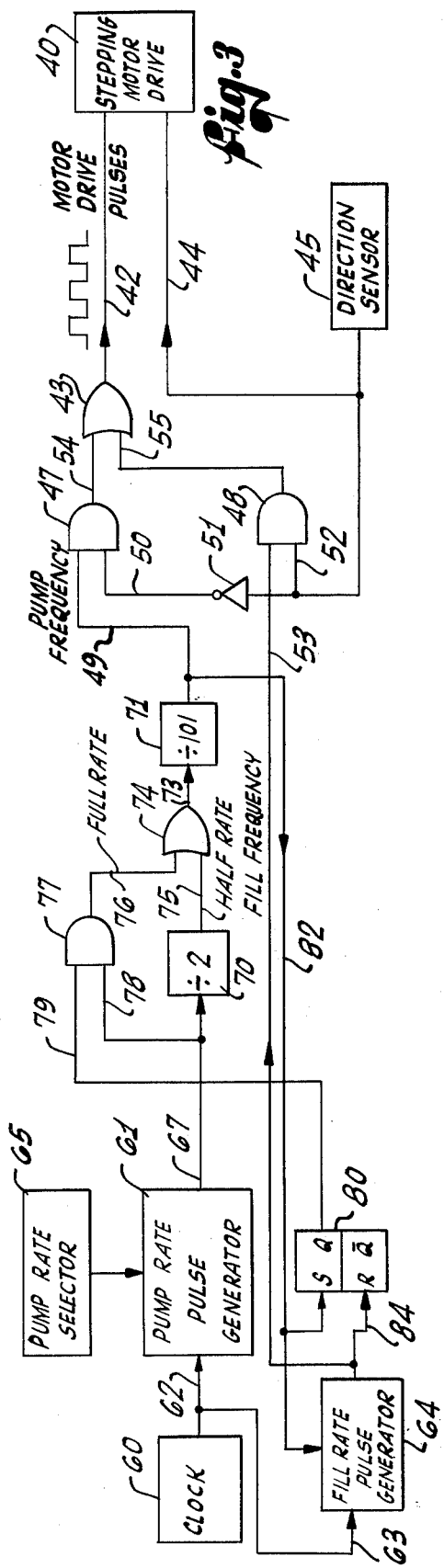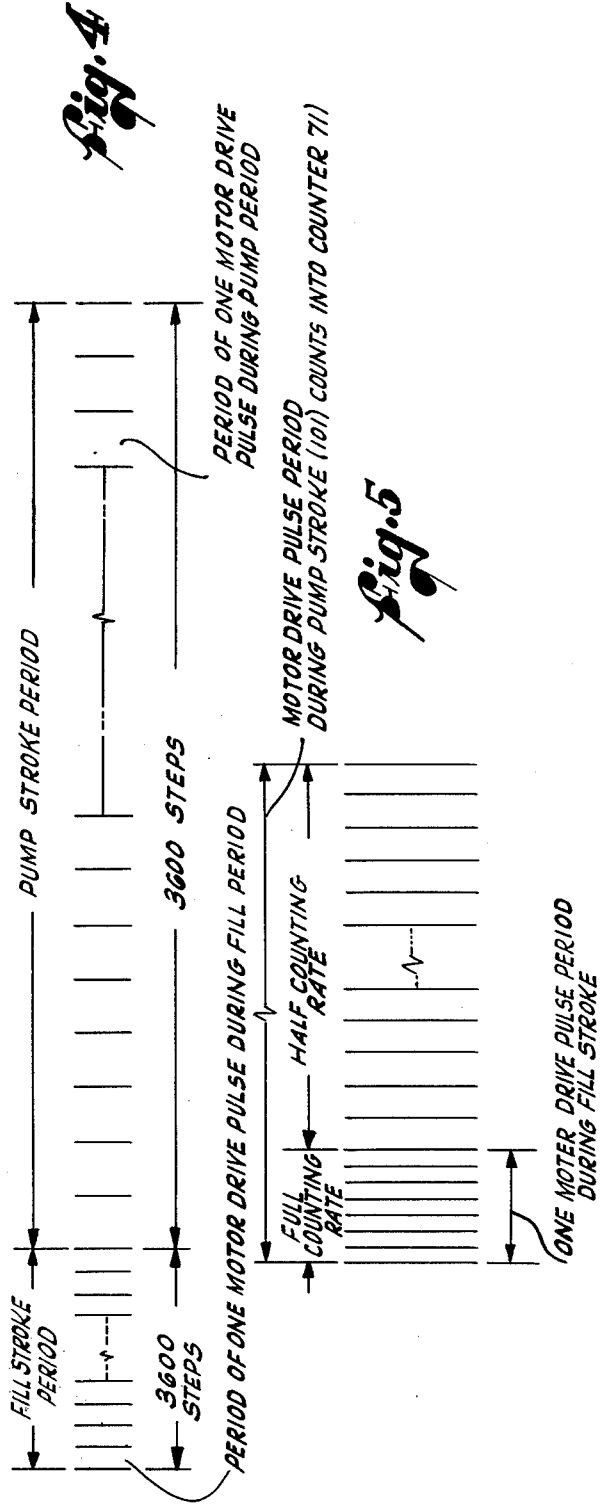

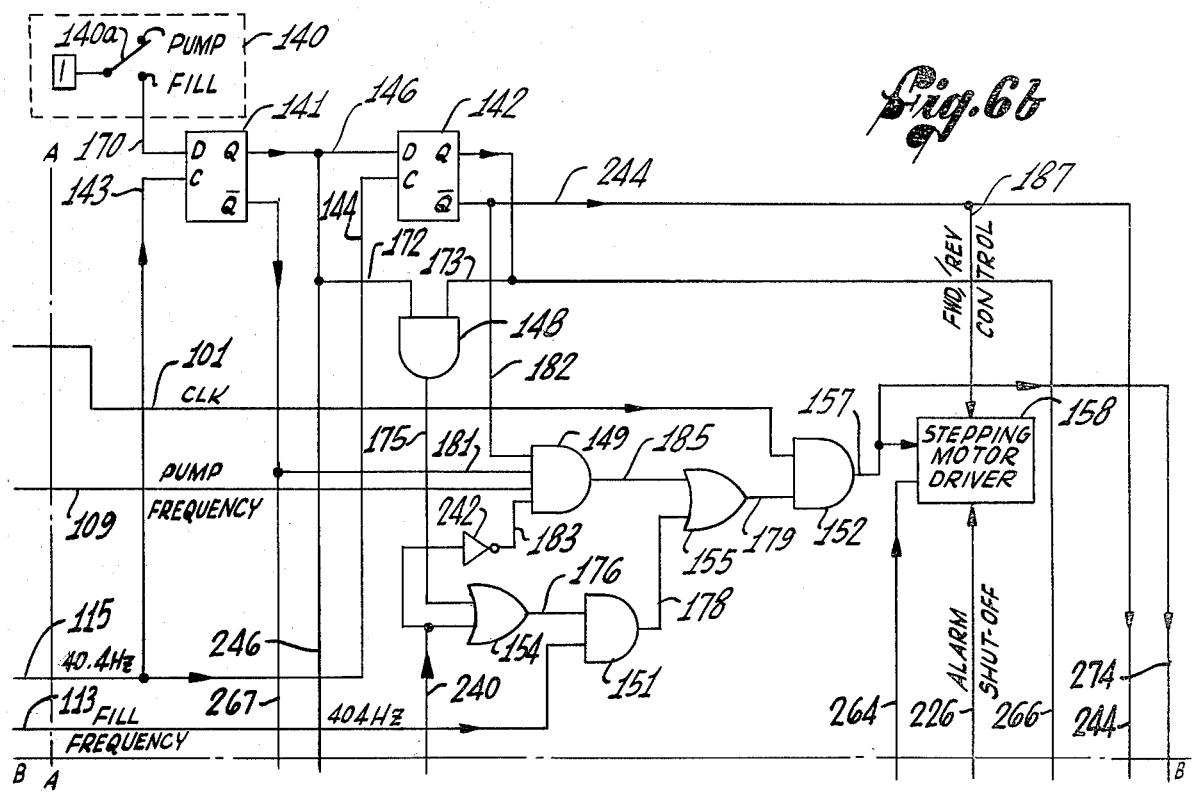
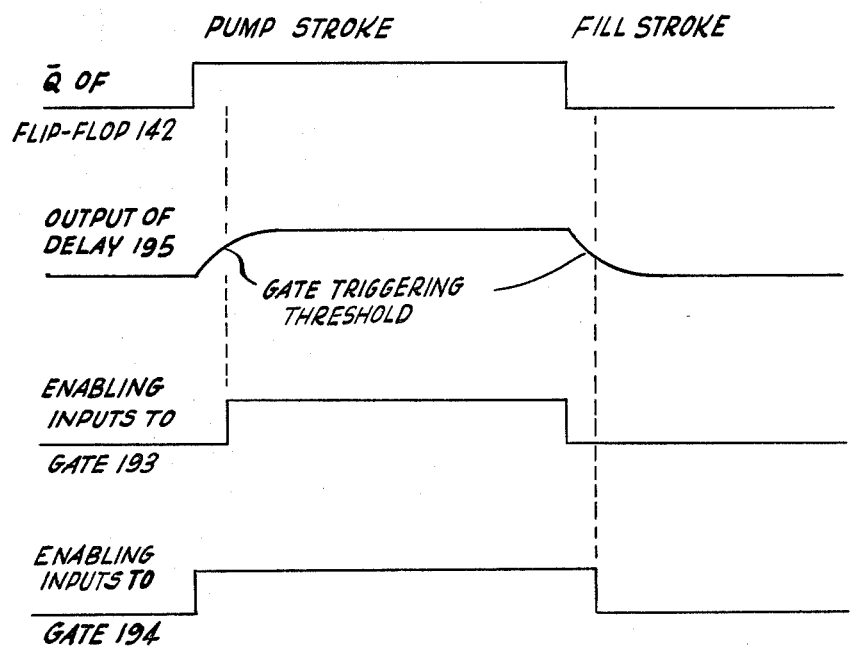

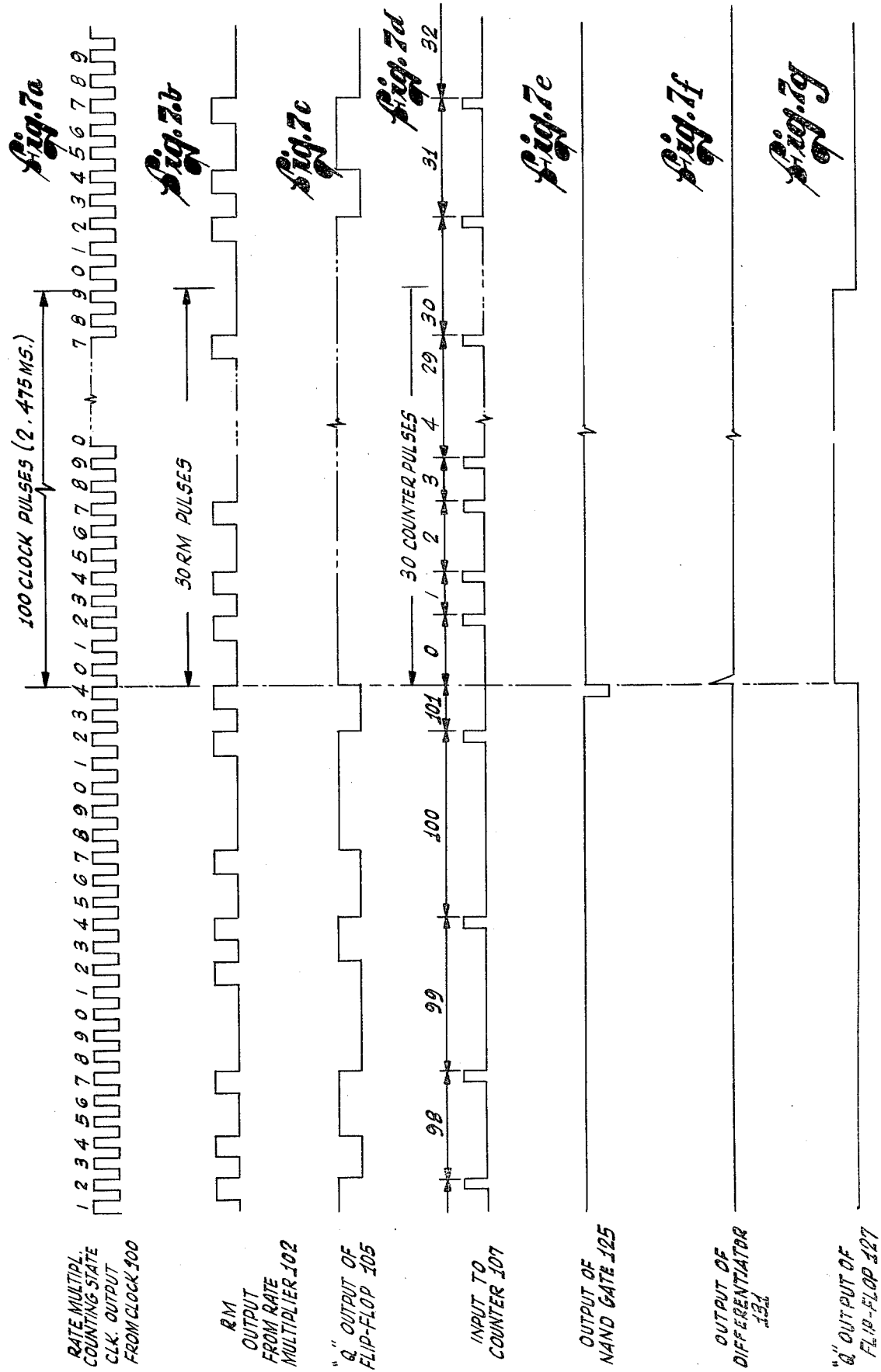

FLUID FLOW CONTROL SYSTEM

BACKGROUND OF THE INVENTION

This invention relates generally to improvements in fluid flow control systems and, more particularly, to a new and improved automatic, highly accurate, positive pressure infusion pump of the syringe pump type, for parenteral administration of medical liquids over a wide range of fluid flow rates.

The usual medical procedure for the gradual parenteral administration of liquids into the human body, such as liquid nutrients, blood or plasma, makes use of apparatus which is commonly referred to in the medical arts as an intravenous administration set. The intravenous set usually comprises a bottle of liquid, normally supported in an inverted position, an intravenous feeding tube, typically of clear plastic, and a suitable valve mechanism, such as a roll clamp, which allows the liquid to drip out of the bottle at a selectively adjustable rate into a transparent drip chamber below the bottle. The drip chamber serves the dual function of allowing a nurse or other attendant to observe the rate at which the liquid drips out of the bottle, and also creates a reservoir for the liquid at the lower end of the drip chamber to insure that no air enters the main feeding tube leading to the patient.

While observation of the rate of drop flow via the drip chamber is a simple way of controlling the amount of liquid fed to a patient over a period of time, its ultimate effectiveness requires that a relatively constant vigil be maintained on the drop flow, lest it cease entirely due to exhaustion of the liquid supply or become a continuous stream and perhaps increase the rate of liquid introduction to the patient to dangerous levels.

By way of example, it has been the general practice in hospitals to have nurses periodically monitor drop flow rate at each intravenous feeding or parenteral infusion station. Such monitoring of drop flow is a tedious and time consuming process, prone to error and associated, possibly serious consequences, and resulting in a substantial reduction of the available time of qualified medical personnel for other important duties. Typically, the nurse monitoring drop flow rate will use a watch to time the number of drops flowing in an interval of one or more minutes, and she will then mentally perform the mathematics necessary to convert the observed data to an appropriate fluid flow rate, e.g., in cubic centimeters per hour or drops per minute. If the calculated flow rate is substantially different than the prescribed rate, the nurse must manully adjust the roll clamp for a new rate, count drops again, and recalculate to measure the new rate.

Obviously, each of the aforedescribed measurements and calculations and flow rate adjustments usually take several minute's time which, when multiplied by the number of stations being monitored and the number of times each station should be monitored per day, can result in a substantial percentage of total personnel time available. In addition, under the pressure of a heavy schedule, the observations and calculations performed by a harried nurse in measuring and adjusting flow rate may not always prove to be reliable and, hence, errors do occur, resulting in undesired, possibly dangerous infusion flow rates.

In addition to the aforedescribed difficulties, the parenteral administration of medical liquids by gravity induced hydrostatic pressure infusion of the liquid from a bottle or other container suspended above a patient, is very susceptible to fluid flow rate variation due to changes in the liquid level in the bottle, changes in temperature, changes in the venous or arterial pressure of the patient, patient movement, and drift in the effective setting of the roll clamp or other valve mechanism pinching the feeding tube. Moreover, there are a number of situations, such as in intensive care, cardiac and peditric patients, or where rather potent drugs are being administered, where the desired fluid flow rate must be capable of precise selection and must not drift beyond certain prescribed limits. In addition, it is extremely important in such situations for medical personnel to be informed of undesirable fluctuations in flow rate, failure of the fluid delivery system for any reason, leakage of the system, or exhaustion of liquid supply when the bottle is emptied.

It will be apparent, therefore, that some of the most critical problems confronting hospital personnel faced with an overwhelming duty schedule and limited time availability are the problems of quickly, easily, reliably and accurately maintaining proper fluid flow rates in the parenteral administration of medical liquids.

In recent years, a number of electrical monitoring systems, drop flow controllers and infusion pumps have been developed to accomplish the various tasks of monitoring and regulating drop flow rates. Some of these devices have also been capable of activating alarms when a potentially dangerous condition exists, thus freeing medical personnel to some extent, for other duties. However, while such monitoring and drop rate control devices have generally served their purpose, they have not always proven entirely satisfactory from the standpoint of cost, complexity, stability, reliability, accuracy, or precision of adjustment over a wide range of selected fluid flow rates. In addition, such systems have sometimes been subject to drift and substantial flow rate variations due to changes in temperature, feeding tube crimps, variations in venous or arterial pressure of the patient, or variations in the height of the bottle or solution level within the bottle. Substantial difficulties have also been experienced particularly in connection with establishing and maintaining accurate flow at very low flow rates.

Positive pressure pumps of the closed loop peristaltic type have been provided which overcome some of the aforementioned difficulties with regard to drift, and accurate flow at low flow rates. However, even such closed loop positive pressure systems only serve to maintain accuracy of flow in terms of stablizing to a preselected drop flow rate, rather than delivering a precise preselected volume of fluid, e.g., in cubic centimeters per hour. The reason for this is that the accuracy of such systems is limited inherently to the accuracy of the size of the drops produced by an intravenous administration set, and the actual drops produced by the latter apparatus can vary from its designated drop size, e.g., by virtue of drip chamber structural variations, by as much as 30 percent.

Positive pressure infusion pumps of the syringe type have also been provided, wherein a syringe having a precise displacement volume is repeatedly filled and emptied on alternate piston strokes during a combined fill stroke and pump stroke operational cycle, so that control of the rate at which the syringe is filled and emptied provides an accurate means for precise fluid volume delivery within a prescribed period of time. However, since a portion of each operating cycle with such syringe type pumps is concerned with filling the syringe, rather than delivering fluid to the patient in a pumping mode, the accuracy of such devices tends to fall off, particularly at very high flow rates, where the fill stroke period is of significantly large duration relative to the pump stroke period. Attempts have been made to provide various types of non-linear calibration for such syringe type systems, in an attempt to compensate for the lost time error due to syringe "fill" time in each complete pumping cycle. However, these efforts, at best, have only reduced the degree of inaccuracy in certain limited flow rate ranges, e.g., at low flow rates, and have failed to provide a uniformly high degree of accuracy over a wide range of flow rates, and particularly at very high fluid flow rates.

Hence, those concerned with the development and use of parenteral fluid administration systems, and particularly those concerned with the design of automatic fluid flow control systems, have long recognized the need for improved, relatively simple, economical, reliable, stable and accurate devices for fluid flow control which obviate the aforementioned difficulties. The present invention provides a new and improved fluid flow control system in the form of a syringe pump which clearly fulfills this need.

SUMMARY OF THE INVENTION

Briefly, and in general terms, the present invention provides a new and improved system for accurately controlling fluid flow in the parenteral administration of medical liquids, wherein the frequency of electrical output pulses which energize a stepping motor to drive a syringe cartridge through repetitive cycles of successive fill and pump strokes, is automatically corrected during the pump stroke of each cycle to compensate for the time lost during the fill stroke of each cycle. This is automatically accomplished during generation of each individual motor drive pulse for the pump stroke by accelerating the counting up of the increments defining each pump stroke motor drive pulse period during a portion of each such period equal in duration to a fill stroke motor drive pulse period.

The displacement volume of the syringe cartridge is identical for the fill stroke and for the pump stroke. Therefore, an identical number of discrete steps or motor drive pulses energizing the stepping motor, (typically 3600 steps) is required for each fill stroke during which the syringe is filled with liquid from a fluid source, and for each pump stroke during which the syringe is emptied of its contents and the precise volume of liquid within the syringe is delivered under positive pressure to a patient.

The frequency of the motor drive pulses during the fill stroke is a fixed, predetermined frequency selected to fill the syringe as rapidly as possible without creating a vacuum which might suck air into the syringe. Desirably, the fill period is as short as possible, so that its influence on the overall time for each complete operational pump cycle is minimal. However, as pump rates increase, the pump stroke period becomes shorter and, hence, the time lost during the fill stroke period becomes more and more significant in terms of its effect upon the average fluid flow rate actually delivered by the pump.

In accordance with one aspect of the invention, each motor drive pulse generated during the pump stroke is established by a plurality of smaller increments defined by a counter counted up at a pulse frequency which is automatically varied to compensate each individual motor drive pulse during the pump stroke for the time lost in generating one of the motor drive pulses during a corresponding fill stroke. In this regard, the pulse rate counting up the counter is doubled during the generation of each pump stroke drive pulse period, for that portion of each pump drive pulse period which is equal to a single fill stroke drive pulse period.

The system for establishing the frequency of the drive pulses to the stepping motor is an open loop digital command system embodying a digital pulse generation and rate selection subsystem wherein a preselected pulse frequency, representing the desired flow rate to the counter defining each motor drive pulse period during a pump stroke, is directly proportional to the desired output flow rate, whereas the drive pulse at the output of the counter represent a non-linear compensated function corrected for the time lost during the "fill" portion of each combined "fill" and "pump" operational cycle. The compensated output drive pulses are at a frequency which produces an average fluid flow pumping rate over successive pumping cycles equal to the desired flow rate.

In this regard, while the instantaneous fluid flow pump rate produced during the pump stroke, in a non-compensated system, would be directly proportional to the speed of the stepping motor driving the pump, the average pump rate over longer time periods which includes "fill" periods as well as "pump" periods would not be proportional to the motor speed because of the time lost for filling the syringe. One possible way of correcting for the lost "fill" time in each operational cycle of the syringe pump would be to pump twice as fast as the desired average pump rate during a time period equal to a fill stroke, after each filling of the syringe. The latter procedure is undesirable since it would obviously provide pumping periods at twice the desired rate and, consequently, non-uniform dosimetry characteristics which may not be tolerable with some forms of chemotherapy.

The more desirable approach, in accordance with the present invention, and in contrast to compensation for fill time by pumping twice as fast during the first part of the pump stroke for the same amount of time used to fill the syringe in the fill stroke, e.g., nine seconds, is to spread the frequency correction over the entire pump stroke period, in a manner which provides uniform compensation, individual motor pulse by individual motor pulse.

It takes an equal number of steps of the stepping motor drive to fill and to empty the syringe in the fill and pump stroke periods because the stroke length or travel of the syringe piston is identical in both directions. Instead of running the stepping motor twice as fast for a period equal to the fill stroke, what is done instead is to shorten each pump stroke motor drive pulse period (i.e., increase the motor drive pulse frequency) by the same ratio as the total pumping period would be reduced due to the faster running. This is accomplished by using a frequency divider or counter to generate the motor drive pulses. The divider receives an input pulse frequency proportional to the desired pumping rate and this defines the clocking frequency for the counter. The output frequency of the divider is a pulse train representing the stepping rate of the motor, with one output pulse for each stepped rotational increment of the motor. After each step, the input frequency to the divider is doubled for a time period equal to the stepping period of the motor in the fill stroke. This causes the divider output period, and hence the period of each pump stroke motor drive pulse, to be shortened by the proper ratio, since each fill step has an equivalent pump step. Morover, since every motor drive pulse in the pump stroke is compensated in the aforedescribed manner for the time lost during the fill stroke, the entire fill stroke correction is spread over the entire pump stroke rather than distorting the pumping rate excessively over a lesser portion of the pump stroke.

More specifically, and by way of example, the electrical output of a high frequency clock is directed to a variable rate multiplier controlled by a bank of rate selector switches which are adjusted to provide an output pulse train from the rate multiplier proportional to the desired fluid flow rate. The clock also feeds a pulse generation network which provides an output pulse train at a predesignated, fixed frequency of the motor stepping pulses for the fill stroke. The latter fill frequency pulse generation network may also be conveniently derived from the same rate multiplier used to select the pump frequency. A divider network, e.g., a 101 counter, is used to divide down and therefore smooth out the output pulse frequency from the rate multiplier, a motor drive pulse being generated each time the counter overflows.

Two systems are provided for counting up the counter, one at the full pulse rate from the rate multiplier, the other at half of the pulse rate from the rate multiplier.

The fill frequency is utilized to generate motor drive pulses directly, whenever an appropriate direction sensor indicates that the motor is about to rotate in the direction defining the fill stroke. When the direction sensor indicates initiation of a pump stroke, the fill frequency motor drive pulses are gated off and the drive pulses generated at the pump frequency determined by the divider network are gated on. However, the frequency of the motor drive pulses produced at the output of the divider is a function not only of the pulse rate output from the rate multiplier, but also is a function of the pulse gating input to the counter which determines the rate at which the counter is counted up, and the latter is exclusively under the control of the fill frequency subsystem. In this connection, the maximum counting rate is gated on to count up the counter twice as fast immediately after each motor pulse in the pump stroke, for a time period which is equal to the fill frequency pulse period, i.e., equal to a motor drive pulse in the fill stroke. Upon completion of the time interval defined by a fill pulse period during the first portion of the counting period defining a pump motor drive pulse period, the maximum counting rate is gated off and the half rate is gated on for the remainder of the counting period, thus providing a motor pulse by motor pulse uniform compensation during the entire pump stroke of each operational cycle.

Hence, the pulse frequency out of the divider network is the motor stepping frequency during the pump stroke and this frequency is increased by counting up the divider network twice as fast for the first portion of each counting cycle for a period equal to a single motor pulse period during the fill stroke of the operational cycle.

Several additional subsystems are also provided to insure proper operating conditions. In this regard, a start-up subsystem insures that the pumping system is in the proper position for loading a syringe cartridge, and that the cartridge has been actually installed in the proper manner prior to initiation of a fill and pump cycle. To this end, a syringe detector indicates absence of a syringe cartridge and brings the syringe piston actuator mechanism to the proper position for loading a syringe catridge when the power is initially turned "on". When the syringe is properly installed, special initializing logic latches out the alarm system and initiates normal fill and pump stroke operation.

In addition, appropriate alarms respond to improper operating conditions such as leakage of fluid from the source during the pump stroke, an exhausted fluid source or insufficient fluid flow during the fill stroke, a stalled motor, the detection of air bubbles in the I.V. line, lack of fluid flow due to system component failure, or the occurrence of a runaway pumping state due to system component failure.

Leakage detection during the pump stroke is accomplished by the detection of drop flow between the pump and the fluid source during the pump stroke, since such drop flow should only be detected during the fill stroke.

Leakage detection during the fill stroke, or the indication of an empty bottle, is accomplished via a drop rate discriminator. Since the rate of fill of the syringe is fixed, any indication that the drop rate has fallen below a prescribed level during the fill stroke would indicate that the fluid source has either become exhausted, or that a leak exists between the fluid source and the pump.

The presence of a stalled motor condition is detected by a rotation sensor which normally resets a counter counting the motor drive pulses.

The existence of air bubbles in the I.V. line is detected by a photocell and reference light beam combination, the light beam being interrupted by the passage of bubbles, to generate an output signal from the photocell.

The absence of fluid flow due to component failure is accomplished by an accumulator-discriminator which is charged up by signals from the drop detector. At the end of the fill stroke, the accumulator charge is sensed, and the stepping motor is shut off if the charge is too low.

A high rate alarm, indicative of a runaway pumping state due to system component failure is provided by a rate meter-comparator combination which generates a current proportional to the frequency of the motor drive pulses and compares that current with a current representing the high order rate multiplier selection switches. If the current sensed by the rate meter exceeds the current generated by the setting of the rate selector switches, the system is put into alarm and the stepping motor is shut off.

The new and improved fluid flow control system of the present invention is extremely accurate, reliable and easy to use. The system provides enhanced precision in selecting and maintaining extremely accurate fluid flow rates over a wide range, and the system is quick to inform medical personnel of any conditions which might pose a hazard to the patient.

These and other objects and advantages of the invention will become apparent from the following more detailed description, when taken in conjunction with the accompanying drawings of illustrative embodiments.

DESCRIPTION OF THE DRAWINGS

FIG. 3 is a combined block diagram and electrical schematic of a simplified system for compensating motor drive pulses generated during the pump stroke for time lost during the fill stroke;

FIGS. 4 and 5 are graphical representations illustrating the basic motor drive pulse compensation concepts of the present invention;

FIGS. 6a, 6b and 6c are combined block diagrams and electrical schematics of one embodiment of an overall fluid flow control system in accordance with the present invention, FIG. 6a being primarily directed to the stepping motor drive pulse generation and compensation subsystems, FIG. 6b being primarily directed to the motor direction and speed control subsystems, FIG. 6c being primarily directed to the start-up and alarms subsystems;

FIGS. 7a–7g are waveforms for various portions of the pulse generation and control subsystems in the overall system of FIGS. 6a, 6b and 6c; and FIGS. 8a–8d are graphical representations illustrating various electrical states relating primarily to operation of the alarms subsystem in the overall system of FIGS. 6a, 6b and 6c.

DESCRIPTION OF THE PREFERRED EMBODIMENT

Figure 1:
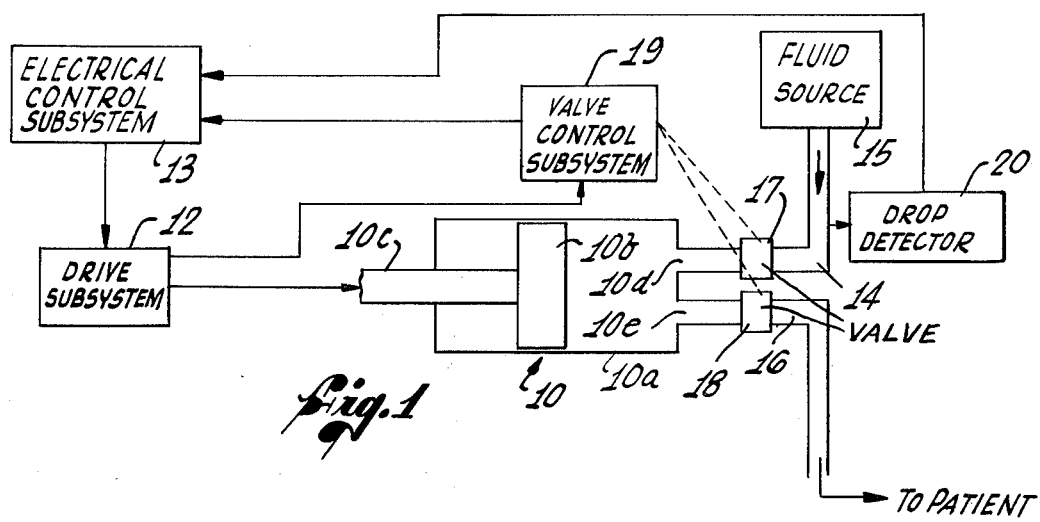
FIG. 1 is a generalized block diagram of an overall system for a syringe pump of the type used in practicing the present invention.

Referring now to FIG. 1 of the drawings, there is shown an overall system for fluid flow control, capable of embodying features of the present invention. In the ensuing description, while reference is made to the term "I.V.", normally connoting intravenous administration, it is to be understood that this is by way of example only, and the flow control system of the present invention is suitable for other forms of parenteral administration as well as intravenous administration.

The system shown in FIG. 1 depicts a syringe pump embodying a syringe 10 which preferably is in the form of a disposable cartridge, but it will become apparent that many features of the present invention may be practiced independently of whether or not the syringe 10 is disposable. The syringe 10 is typically fabricated of molded plastic and essentially includes a cylinder 10a in which a piston 10b is slidably received and adapted to be reciprocated back and forth along the axis of the cylinder by an integral piston rod 10c which is coupled to and appropriately driven by a suitable drive subsystem 12. The drive subsystem 12 typically includes a reversible d.c. stepping motor driving, through appropriate gearing, a lead screw which is, in turn, coupled to the piston rod 10c of the syringe 10. The d.c. stepping motor of the drive subsystem 12 is energized by a pulse train of motor drive pulses generated by an electrical control subsystem 13 and appropriately fed to the drive subsystem.

The syringe 10 includes an inlet port 10d and an outlet port 10e. The inlet port 10d communicates through a suitable I.V. line 14 with any appropriate fluid source 15, typically an I.V. bottle containing appropriate drugs and or nutrients in liquid form. Typically, the I.V. line 14 is part of an I.V. administration set which includes a transparent drip chamber (not shown) in the fluid line between the syringe 10 and the fluid source 15.

A similar I.V. line 16 is connected, at one end, to the outlet port 10e of the syringe 10 and conveys fluid from the syringe to a patient. The syringe 10 and drive subsystem 12 may be of conventional design, as previously indicated, or may be of the form described in co-pending application, Ser. No. 554,230, entitled Syringe Pump Drive System and Disposable Syringe Cartridge, inventor Stephen H. O'Leary, filed Feb. 28, 1975, now U.S. Pat. No. 3,993,061 issued Nov. 23, 1976, and assigned to the same assignee as the present application.

A pair of valves 17, 18, typically of the tube pincher or clamping type, are selectively opened and closed at appropriate times in the overall pumping cycle, under the control of a suitable valve control subsystem 19. The valve 17 controls the inlet port 10d and is open during the fill stroke to enable fluid to be drawn from the fluid source 15, through the line 14, into the syringe 10, the valve 17 being closed during the pump stroke to prevent any fluid from exiting the syringe through the inlet port. The valve 18 controls the outlet port 10e and is open during the pump stroke to enable fluid delivery from the syringe 10 to the patient through the line 16, the valve 18 being closed during the fill stroke.

The valve control subsystem 19 is also driven, through appropriate gearing, by the same drive subsystem 12 used to reciprocate the piston 10b of the syringe 10. The valve control subsystem 19 also provides information to the electrical control subsystem 13 indicating that the syringe 10 is either in the fill stroke or pump stroke, and this information, in turn, enables the electrical control subsystem to establish the proper direction of rotation of the stepping motor in the drive subsystem 12. The valves 17, 18 and valve control subsystem 19 may be conventional design, as previously indicated, or may be of the form described in co-pending application, Ser. No, 554,091, entitled Syringe Pump Valving and Motor Direction Control System, inventor Wallace L. Knute, filed Feb. 28, 1975, now U.S. Pat. No. 3,994,294 issued Nov. 30, 1976, and assigned to the same assignee as the present application.

A suitable drop detector 20 monitors drop flow in the I.V. line 14, at the drip chamber (not shown), to insure that drop flow occurs during the fill stroke of the syringe 10 and that drop flow does not occur during the pump stroke of the syringe. In this regard, drop flow should occur in the drip chamber below the fluid source 15 during the fill period of the syringe cycle, and the absence of such flow is an indication of an exhausted fluid source, e.g., an empty I.V. bottle, or a leak between the fluid source and the syringe 10. In contrast, the absence of such drop flow is a requirement during the pump stroke of the syringe cycle, the presence of drops indicating some kind of leakage, such as improper clamping off of the I.V. line 14 by the valve 17.

The drop detector 20 monitors drop flow in the drip chamber of the I.V. administration set and typically may include a sensor housing (not shown) containing a reference light source located opposite a photocell to define an optical sensing gap therebetween, with a reference light beam normally impinging upon the photocell. The housing is appropriately clamped upon the drip chamber of the I.V. set, with the transparent drip chamber positioned within the sensing gap to intercept the reference beam. A falling drop of liquid within the drip chamber interrupts the reference beam, and a variation in electrical response of the photocell is directed to appropriate circuitry indicating the presence of a drop.

One example of a suitable drop detector 20 is set forth in U.S. Pat. No. 3,596,515, inventor, Richard A. Cramer. While a photocell type drop detector 20 has been described, it will be appreciated that any drop sensing device capable of providing an electrical indication of the detection of a drip may be used without departing from the spirit and scope of the invention.

The electrical output of the drop detector 20 is directed as an input to the electrical control subsystem 13 in connection with a variety of alarms subsystems (not shown in FIG. 1).

The displacement volume of the syringe catridge 10 is determined by the volume swept by the piston 10b on each stroke and is identical for the fill stroke and for the pump stroke. Therefore, an identical number of motor drive pulses from the electrical control subsystem 13 to the drive subsystem 12 is required for each fill stroke during which the syringe is filled with liquid from the fluid source 15, and for each pump stroke during which the syringe delivers its precise volume of liquid under positive pressure to a patient. The number of motor drive pulses energizing the stepping motor of the drive subsystem 12 for a complete stroke in either direction, either for the fill stroke or for the pump stroke, is typically 3600 steps in a presently preferred embodiment of the invention.

The frequency of the motor drive pulses during the fill stroke is a predetermined, fixed frequency, typically 404 Hz., selected to rapidly fill the syringe 10 as quickly as possible without creating a vacuum which might suck air into the syringe or which might create a continuous stream (as opposed to flow in discrete drops) in the drip chamber. Preferably, the time interval for performance of a fill stroke (hereinafter referred to as the fill stroke period) is as short as possible so that its influence on the overall time for each complete operational cycle of the syringe 10 is minimal. However, as the desired fluid output pumping rate increases, the pump stroke period becomes shorter and, hence, the time lost during the fill stroke period becomes more and more significant in reducing the actual average fluid flow rate of delivery by the pump.

In accordance with the invention, the motor drive pulses to the stepping motor of the drive subsystem 12 are increased in frequency during the pump stroke of each operational cycle of the pump to compensate for the time lost during each corresponding fill stroke of each operational cycle. The entire fill stroke period correction is spread over the full pump stroke period by compensating each and every individual motor pulse during the pump stroke period for a uniform portion of the time lost during the immediately preceding fill stroke. To accomplish this, the electrical control subsystem 13 counts up the increments defining each pump stroke motor drive pulse twice as fast for the first portion of the counting equal in time to the duration of a motor pulse period generated during the fill stroke of the operational cycle.

The compensated output motor drive pulses from the electrical control subsystem 13 to the drive subsystem 12 are, therefore, at a frequency which produces an average pumping rate over successive pumping cycle equal to the desired fluid flow rate.

Figure 2:
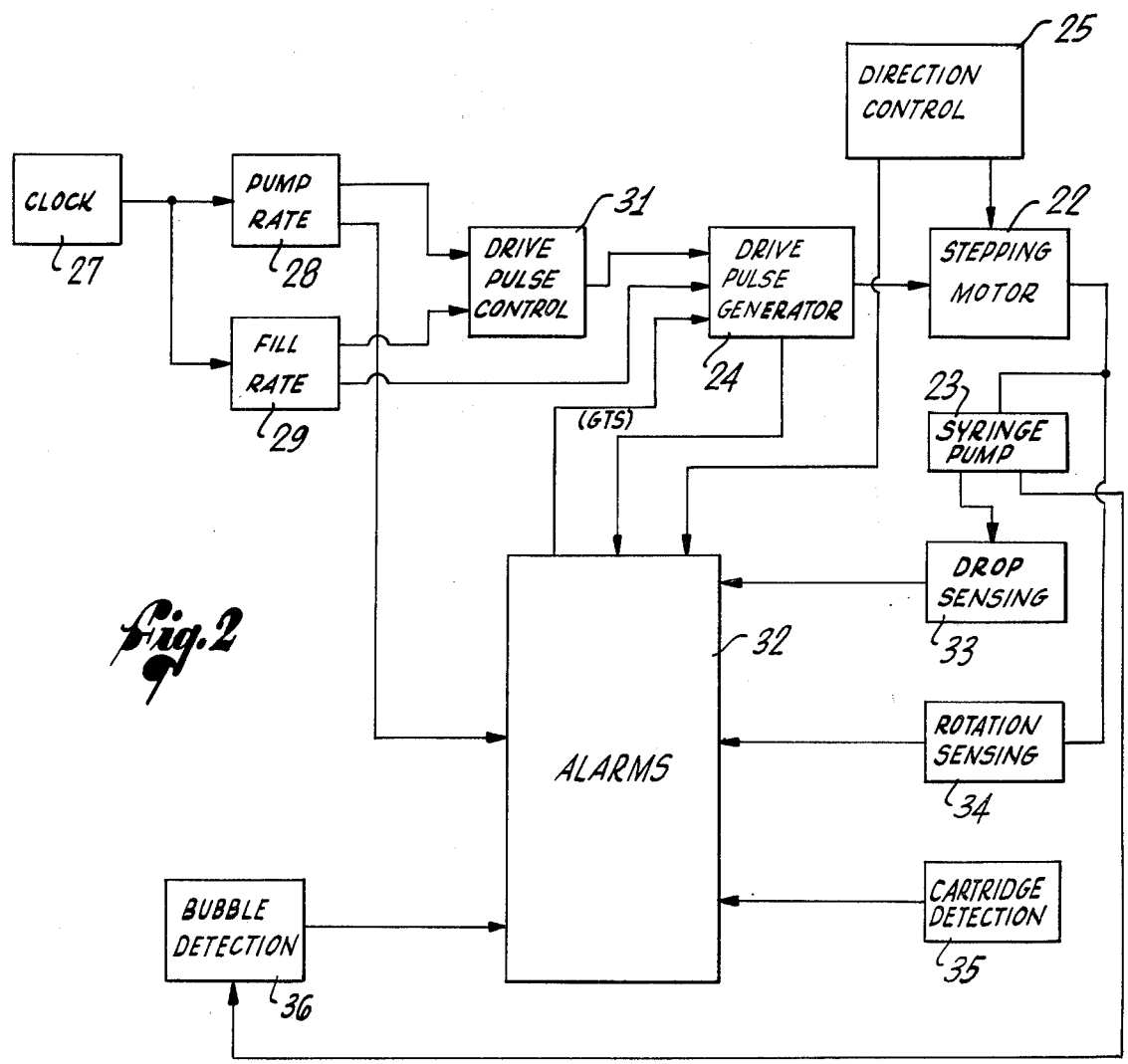
FIG. 2 is a block diagram of an overall electrical system in which some of the basic concepts of the fluid control system of the present invention are embodied.

Referring now to FIG. 2, there is shown a new and improved electrical control system embodyng various features of the present invention.

A d.c. stepping motor 22 drives a suitable syringe pump 23, such as that of the general type shown in FIG. 1. The stepping motor 22 is energized by motor drive pulses received from a drive pulse generator subsystem 24, and the direction of rotation of the stepping motor to produce either a fill stroke or a pump stroke is established by a direction control subsystem 25.

A suitable high frequency clock 27 drives a pump rate determining subsystem 28 and a fill rate determining subsystem 29. The fill rate subsystem 29 feeds the drive pulse generator subsystem 24 directly during the fill stroke period of the syringe pump cycle and, therefore, produces motor drive pulses at the output of the pulse generator subsystem 24 at a fixed fill rate frequency. In contrast, the pump rate subsystem 28 feeds an intermediate drive pulse control subsystem 31 which, in turn, energizes the drive pulse generator subsystem 24.

The drive pulse control subsystem 31 also receives a controlling input from the fill rate subsystem 29. In this connection, when the syringe pump operational cycle is in the pump stroke period, the drive pulse control subsystem 31 provides a pulse output to the drive pulse generator subsystem 24 which is compensated for the lost time during the fill stroke period to provide an output pulse train from the pulse generator which will maintain an average fluid flow rate equal to the desired fluid flow rate. This is accomplished by having the fill rate subsystem 29 dominate the drive pulse control subsystem 31 for the first portion of each motor drive pulse period of the pump stroke equal to a motor drive pulse period in the fill stroke. During this first time interval of each pump stroke motor drive pulse, the drive pulse control subsystem 31 is counted up at twice the frequency as that which is used to count up the control subsystem for the remaining portion of the motor drive pulse period. Therefore, the output of the drive pulse control subsystem 31 and, hence, the motor drive pulse output from the pulse generator subsystem 24 is at a higher frequency over the entire pump stroke period of the operating cycle than would otherwise be provided if the pump rate subsystem 28 drive the subsystem 24 directly without its output being first compensated for the time lost during each fill stroke.

An alarms subsystem 32 receives input from a drop sensing subsystem 33 for appropriate leakage or empty bottle detection, a rotation sensing subsystem 34 for detecting a stalled stepping motor 22, a syringe cartridge detection subsystem 35 to determine whether an appropriate syringe cartridge has been properly installed prior to initiation of pump operation, and a bubble detecting subsystem 36 to determine if there is air in the I.V. line. The alarms subsystem 32 also receives inputs from the pump rate determining subsystem 28, the drive pulse generator subsystem 24 and the direction control subsystem 25, so that other alarm functions can be performed with knowledge of the particular portion of the operational cycle in effect, e.g., fill stroke, pump stroke, or the transient state between either of these strokes. The alarms subsystem also responds, with the inputs shown in FIG. 2, in the event of component failure somewhere in the pumping system which may produce a lack of fluid flow or induce a runaway pumping state generating an uncalled for high pumping rate.

Referring now to FIG. 3, there is shown a simplified system for compensating the frequency of stepping motor drive pulses generated during the pump stroke period for the time lost during the fill stroke period.

A stepping motor drive 40 for the syringe pump, typically embodying a d.c. stepping motor (not shown), receives appropriate incremental drive pulses over line 42 which is the output of a drive pulse OR gate 43. The stepping motor drive 40 also receives an input over line 44 from a suitable direction sensor 45 (typically in the valve subsystem for the syringe pump) which conditions the stepping motor direction of rotation so that the drive pulses recieved over line 42 will step the motor either in the direction to perform a fill stroke or in the direction to perform a pump stroke.

The direction sensor 45 also determines whether the output pulses appearing on line 42 are at the fill frequency or at the pump frequency. In this regard, the system of FIG. 3 includes an AND gate 47 which is the control gate for the output of pump frequency motor drive pulses and a second AND gate 48 which is the control gate for the output of fill frequency motor drive pulses.

The pump frequency control gate 47 receives as one input over line 49 a pump frequency pulse train, and receives as a second enabling input over line 50 the inverted electrical output of the direction sensor 45. The latter is accomplished by directing the output of the direction sensor 45 through an inverter 51 to the gate 47.

The output of the direction sensor 45 is also directed as an enabling input, over line 52, as one input to the fill frequency control gate 48, the other input to the gate 48 being the fill frequency pulse train over line 53.

Hence, it will be apparent that the direction sensor 45 selectively enables either the pump frequency control gate 47 or the fill frequency control gate 48, depending upon whether or not a pump stroke or a fill stroke is about to be performed by the syringe pump. The output pulses from the control gates 47 or 48 are directed over lines 54, 55, respectively, as inputs to the drive pulse gate 43 which, in turn, passes motor drive pulses to the stepping motor.

A suitable high frequency clock 60 feeds a pump rate pulse generator 61 over line 62 and a fill rate pulse generator 64 over line 63. The pump rate pulse generator 61 is typically a rate multiplier and is under the control of a pump rate selector 65, typically in the form of rate selector switches for the rate multiplier.

The electrical output of the pump rate pulse generator 61, over line 67, is a pulse train directly proportional to the desired instantaneous fluid flow rate delivered by the syringe pump during the pump stroke period of the syringe pump operational cycle. However, as previously indicated, the average fluid flow rate delivered by the syringe pump, in the absence of compensation, will be less than the desired fluid flow rate and will be a non-linear function of the selected pulse rate produced by the pulse generator 61, because of the time lost during the fill stroke period of the operational cycle.

The fill rate pulse generator 64 may be a separate subsystem for dividing down the clock frequency to the desired fill frequency or it may conveniently be derived from the appropriate high order decades of the pump rate pulse generator rate multiplier. For purposes of simplicity, however, the fill rate pulse generator 64 is shown as a separate divider subsystem. The fill frequency pulse train generated by the pulse generator 64 is directed as electrical input over line 53 to the fill frequency control gate 48 which passes the pulse train to the drive pulse OR gate 43 whenever the direction sensor 45 calls for performance of a fill stroke.

In order to smooth out the electrical output of the pumprate pulse generator 61, a divider network is provided which includes a divide-by-two counter 70 and a divide-by-101 counter 71, thus dividing the output of the pulse generator 61 by a total of "202". Overflow of the counter 71 at the count of "101", produces a pump frequency motor drive pulse over line 49 to the control gate 47 which passes the pump frequency pulse train over line 54 through the drive pulse OR gate 43 whenever the direction sensor 45 calls for performance of a pump stroke.

The manner in which the pump frequency is compensated for time lost during the fill stroke period, to make the average flow rate equal to the desired flow rate selected by the pump rate selector 65, is next described. In this regard, the divide-by-two counter 70 is selectively bypassed, under control of the fill frequency pulse train, to count up the counter 71 at twice the normal rate during the first portion of each motor drive pulse period for a pump stroke equal in time to a motor drive pulse period for a fill stroke. To this end, the "101" counter 71 is counted up by counting pulses recieved over line 73 from an OR gate 74 which receives a pair of inputs over lines 75, 76. The pulse rate on line 75 is one-half of the pulse rate on line 76, the former pulse rate being the output of the divide-by-two counter 70, whereas the latter count rate is the full pulse rate output from the pulse generator 61 with the divide-by-two counter 70 bypassed. In this regard, the AND gate 77 bypasses the counter 70 and receives the output of the pump rate pulse generator 61 over line 78. The gate 77 also receives an enabling input over line 79 from a control flip-flop 80. The AND gate 77 is enabled each time the Q output of the control flip-flop 80 is "true", and the gate 77 is disabled whenever the Q output of the flip-flop 80 is "false".

Each time the counter 71 overflows, generating a pump frequency motor drive pulse, it also resets the fill rate pulse generator 64 and sets the control flip-flop 80, over line 82, so that its Q output is "true". Hence, the output of the pump rate pulse generator 67 bypasses the divide-by-two counter 70, through the AND gate 77 and OR gate 74, until such time as the AND gate 77 is disabled by the control flip-flop 80. In this connection, the "reset" input of the control flip-flop 80 is under the control of the fill rate pulse generator 64, over line 84. Thus, the AND gate 77 will be disabled, by the Q output of the control flip-flop 80 going "false", at the end of a single fill rate pulse period which resets the flip-flop 80.

In summary, the fill rate pulse generator 64 directly provides output motor drive pulses over line 53, through gates 48 and 43, during the fill stroke period of the syringe pump operational cycle. However, during the pump stroke period of the operational cycle, the motor drive pulses are defined by the overflow of a divider network which simultaneously functions to smooth out the pulses from the pump rate pulse generator 61 and also compensates the motor drive pulse frequency for time lost during the fill stroke period. This is accomplished by counting up the "101" counter 71 at twice the rate during the first portion of each pump stroke motor drive pulse period for a time interval equal to a fill stroke motor drive pulse, under the control of the fill rate pulse generator 64, control flip-flop 80 and AND gate 77, after which the gate 77 is disabled and the pulse rate from the pump rate pulse generator 61 is divided in half by the counter 70 prior to being fed through the OR gate 74 to the counter 71. The result is a uniform, motor pulse by motor pulse compensation for time lost during the fill stroke period, the compensation being spread over the entire pump stroke period.

FIGS. 4 and 5 graphically illustrate the basic motor drive pulse frequency compensation technique accomplished by the system of FIG. 3. In FIG. 4, it will be apparent that the fill stroke period and the pump stroke period are defined by an equal number of motor drive pulse steps, e.g., 3600 steps in a presently preferred embodiment of the invention, since the pump stroke and fill strokes are identical except for direction. However, the period of a single motor drive pulse during the pump stroke is at least equal to or greater than the period of a single motor drive pulse during the fill stroke, i.e., the fill frequency is equal to or greater than the maximum contemplated pump frequency.

Referring now more particularly to FIG. 5, there is shown an enlarged view (on a time scale) of the period of a single motor drive pulse during a pump stroke. The latter period is defined by a total of 101 counts into the counter 71 in the system of FIG. 3. Note that, for the first portion of the counter cycle, equal in time duration to a motor drive pulse period during a fill stroke, the counter 71 is counted up at twice the counting rate as during the remainder of the counting cycle defining the pump stroke motor drive pulse. Hence, during the first part of the pulse period, the counter 71 is counted up by the full pulse rate output of the pump rate pulse generator 61 in FIG. 3, whereas for the balance of the counting cycle defining the pump stroke motor drive pulse period, the output of the pulse generator 61 passes through the divide-by-two counter 70, thereby cutting the counting frequency in half.

Figure 6A:
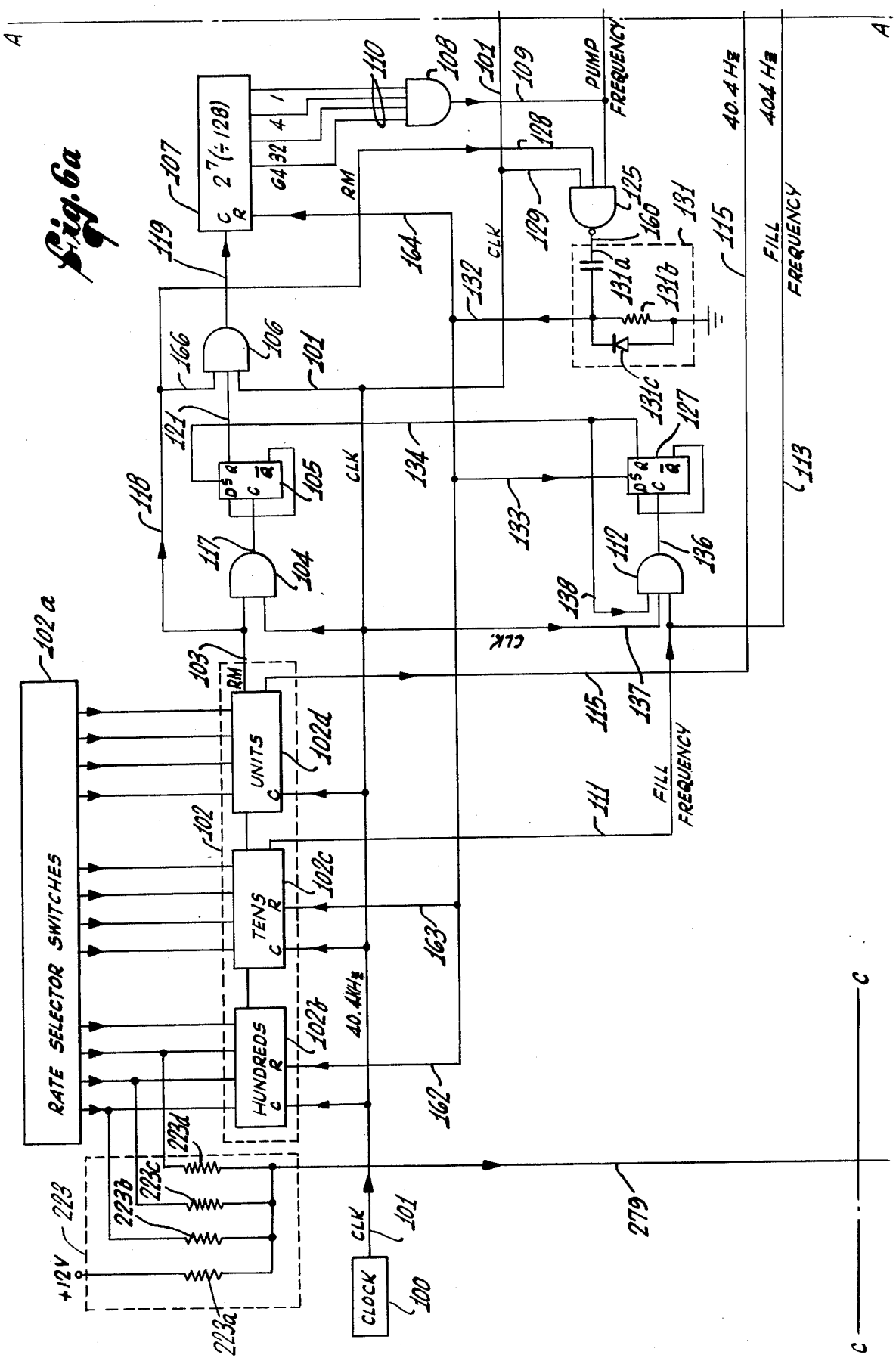
Figure 6C:
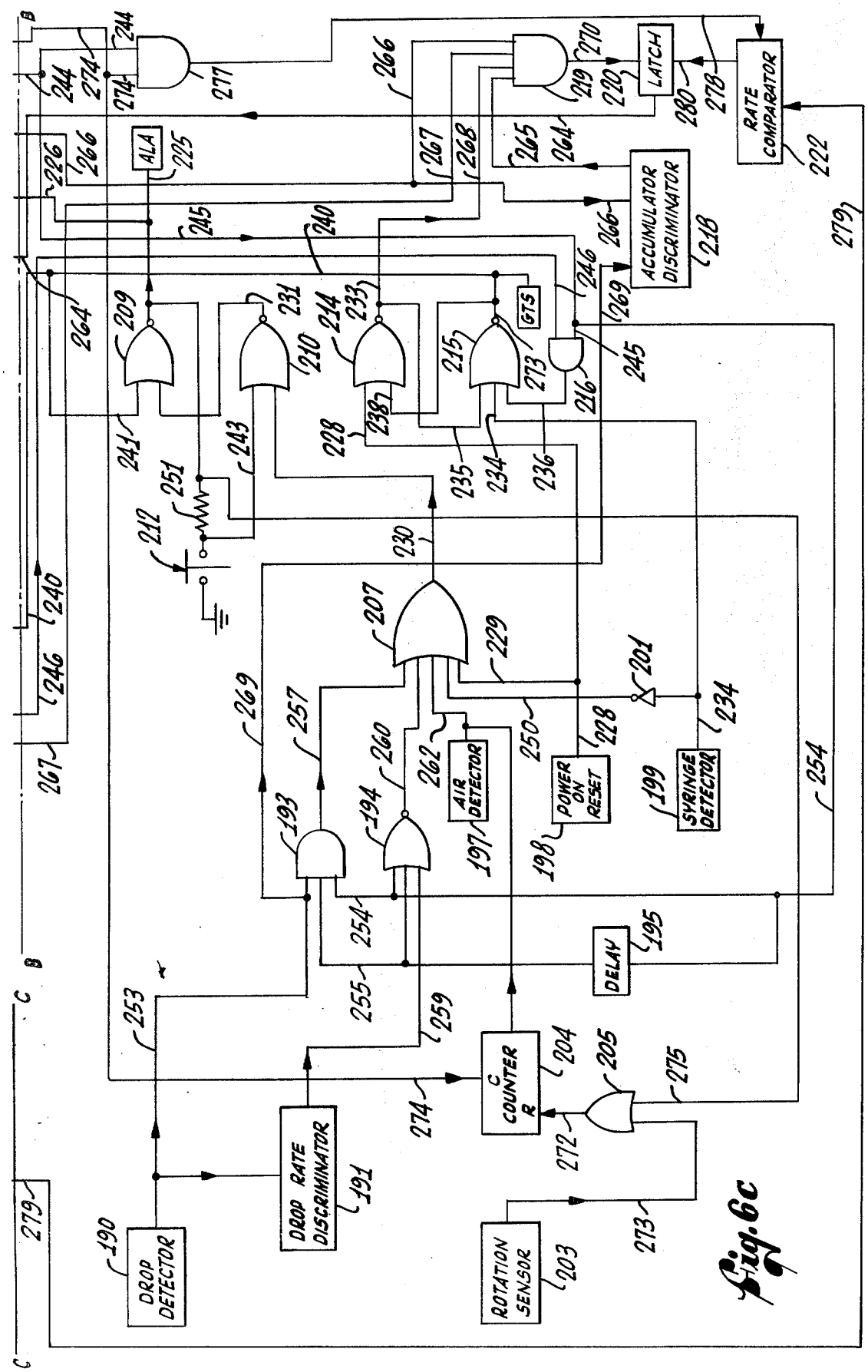

FIGS. 6a, 6b and 6c are combined block diagrams and electrical schematics of one embodiment of an overall fluid flow control system for accomplishing the aforedescribed motor drive pulse frequency compensation technique and providing a number of additional features regarding proper system conditioning for receipt of a syringe cartridge prior to initiation of an operational cycle, as well as the provision of appropriate alarm safeguards. FIGS. 6a, 6b and 6c are arranged with their respective input and output connections aligned so that the three figures can be used as a single drawing for the entire fluid flow control system. In this regard, the various subsystem electrical connections overlap with each other to such a degree that the system is best described with regard to the combined figures, and the balance of the description will accordingly be made with reference to such a composite drawing.

Prior to a detailed description of the operation of the overall system depicted in FIGS. 6a, 6b and 6c, the main elements of each major subsystem area, and their functions, are first summarized.

FIG. 6a is primarily directed to the frequency generating and compensating sections of the overall system for generating the stepping frequency of the motor and includes, referring to FIG. 2 previously discussed, the clock 27, pump rate determining subsystem 28, fill rate determining subsystem 29, drive pulse control subsystem 31 and portions of the drive pulse generator subsystem 24. The system shown in FIG. 6a has two primary output frequencies, one being the pump frequency for stepping the syringe pump drive motor in the forward direction during the pump stroke, while the other output frequency is the fill frequency which is at a fixed rate and drives the stepping motor drive in the reverse direction during a fill stroke. The fill frequency is also used to bring the piston actuator for the syringe cartridge to its start-up condition for easy insertion of the syringe cartridge into the pumping apparatus when the overall pump system is about to be put into operation.

FIG. 6b relates primarily to the forward-reverse and speed control section of the overall system and, referring again to FIG. 2, primarily includes the stepping motor 22, the direction control subsystem 25, and portions of the drive pulse generator subsystem 24.

FIG. 6c is directed primarily to the details of the alarms subsystem 32 in FIG. 2, and the related input subsystems for the alarms, including the drop sensing subsystem 33, rotation sensing subsystem 34, cartridge detection subsystem 35 and bubble detection subsystem 36, as well as inputs from other appropriate portions of the system necessary to determine the alarm and start-up conditions.

Referring now to FIGS. 6a, 6b and 6c, as a composite system diagram, a conventional high frequency clock generator 100 (FIG. 6a) directs digital pulses (the CLK signal) over line 101 to a conventional digital rate multiplier 102 which embodies a plurality of digital rate selector switches 102a associated therewith for determining the output pulse frequency of the rate multiplier. The clock 100 is the master clock for the entire system and controls the frequencies and timing.

The rate multiplier 102 multiplies the input frequency by a maximum factor of unity. The output of the rate multiplier 102 over line 103 is a digital pulse rate (the RM signal) proportional to the setting of the rate selector switches 102a and, therefore, proportional to the desired output fluid flow rate to which the overall system is intended to stabilize. The electrical output (RM) of the rate multiplier 102 over line 103 is not, however, a continuous pulse train, but rather an irregular burst of pulses, due to the nature of the fractional multiplication which can occur in the rate multiplier. The typically non-uniform pulse train on line 103 is directed through AND gates 104, 106 to a conventional divider network in the form of counters 105 and 107 which serve to smooth out the jitter in the rate multiplier pulse train.

The electrical output of the counter 107 is decoded by an AND gate 108 to produce an output signal on line 109 each time the counter 107 counts to its "101" state. The output pulse train created on line 109 by each "101" counts of the counter 107 is at the compensated pump frequency used to generate the motor drive pulses for the pump stroke and corresponds to the output of the drive pulse control subsystem 31 in FIG. 2.

The clock frequency generated by the clock 100 is, in a presently preferred embodiment of the invention, selected to be 40.4 kilohertz. The fill frequency is conveniently derived from the high order decades of the rate multiplier 102 by dividing the clock frequency by a factor of "100" to produce a fill frequency of 404 Hz. The fill frequency is depicted schematically as electrical pulse output over line 111 from the rate multiplier 102. The latter fill frequency is directed as one input to an AND gate 112 in the drive pulse control subsystem, and is also directed simultaneously over line 113 as an input to the drive pulse generator subsystem (corresponding to the drive pulse generator subsystem 24 in FIG. 2) to control generation of motor drive pulses when the overall system is performing a fill stroke.

The clock frequency (CLK) of the clock 100 is determined by taking into account a number of factors such as the number of motor steps to complete a stroke, the size of the syringe pump chamber, i.e., syringe volume displacement, the number of counting pulses defining a single motor drive pulse period, and the maximum frequency at which the selected stepping motor is designed to operate. Using a fill frequency of 404 Hz., a 5 cubic centimeter displacement volume for the syringe, 3600 steps of the stepping motor to accomplish each syringe stroke and a maximum pump rate of approximately 1000 cc. per hour, a clock frequency of 40.4 kilohertz has been determined to be suitable for the presently preferred embodiment illustrated in FIGS. 6a–6c.

The reason for selecting a count of "101" for the counter 107 as determinative of the pump frequency is directly related to the relationship of the fill frequency to the clock frequency. Since, as previously pointed out, it is essential to the basic compensation technique utilized in the present invention that the pump stroke period be equal to or greater than the fill stroke period (since the compensation period in each pump stroke motor drive pulse must be equal to a fill stroke motor drive pulse period), the requirement for a count of "101", i.e., 101 RM pulses, insures that the pump stroke motor pulse period will always be at least one percent greater than the fill stroke motor pulse period even at the maximum pumping rate. This follows logically since, at the highest pumping rate of approximately 1,000 cc. per hour, the output pulse frequency of the rate multiplier 102 will be equal to the full clock frequency (CLK) of the clock 100. Since the fill frequency of 404 Hz. is obtained by dividing the 40.4 kilohertz clock frequency by a factor of "100", the process of limiting the maximum pump frequency (via the counter 107) to the clock frequency divided by a factor of "101", obviously insures that the maximum pump frequency will be less than the fill frequency by approximately one percent and, hence, the pump stroke period will be longer than the fill stroke period by at least that same percentage at all times.

With a fill frequency of 404 Hz. and 3600 steps of the stepping motor to accomplish each syringe stroke, the fill stroke takes a time period of approximately 9 seconds. The reason for the selection of 9 seconds for the "fill" period is to make the fill period as short as practical, yet avoid pulling so fast as to pull a vacuum on the I.V. tubing and therefore draw air bubbles from the drip chamber into the tubing. In addition, having too high a fill rate can produce a continuous stream in the drip chamber which would cause failure of the drop detection subsystem and, as will subsequently become apparent, would cause the overall system to go into alarm. A further factor involved in determining the fill rate is the consideration of motor power, in that more battery power and a more powerful stepping motor would be required for a higher fill rate. Therefore, it is practical to limit the fill rate to a rate close to the maximum pumping rate required by the system.

The rate multiplier 102 is typically a binary coded decimal rate multiplier having three decades, a "hundreds" decade 102b, a "tens" decade 102c, and a "units" decade 102d, thus enabling selectable fluid flow pumping rates of from 1 to 999 cc. per hour. The electrical output from the "tens" decade 102c over line 111 is, as previously indicated, the fill frequency of 404 Hz.

An additional electrical output, is provided from the "units" decade 102d, over line 115, and is at a frequency of 40.4 Hz. obtained by dividing the clock frequency by a factor of "1,000". The latter 40.4 Hz. frequency is subsequently utilized by the forward-reverse speed control logic as timing pulses to enable the stepping motor to come to a stop and reverse direction, in going from a fill stroke to a pump stroke or from a pump stroke to a fill stroke.

The AND gate 104 controls the feeding of clock pulses, over line 117, to the flip-flop 105. Essentially, the gate 104 gates the RM pulse output from the rate multiplier 102 to the flip-flop 105, in synchronism with the clock 100. The same RM pulse train is also provided, over line 118, as one input to the AND gate 106 which controls the counting input to the counter 107, over line 119. The other inputs to the AND gate 106 are the CLK signal, over line 101, and the Q state of the flip-flop 105 over line 121.

The flip-flop 105, as well as all of the other flip-flops shown in the system of FIGS. 6a–6c are all conventional D-type flip-flops which essentially produce at the Q output of the flip-flop, after the clock pulse, the signal present at the D input of the flip-flop at the time the clock pulse occurred. Hence, the D-type flip-flop introduces a delay of one clock period between the input and the output of the flip-flop.

The AND gate 108, as previously indicated, is an AND gate that decodes out the "101" state of the counter 107 for purposes of generating the compensated pump frequency. The output of the gate 108, on line 109, is also directed as one input to a NAND gate 125 which forms part of the subsystem for generating reset pulses for the rate multiplier 102, counter 107, flip-flop 105 and a compensation control flip-flop 127. In addition to receiving the "101" state as input over line 109, the NAND gate 125 also receives the RM signal over line 128 and the CLK signal over line 129, as additional inputs.

The electrical output of the NAND gate 125 is directed to a differentiator 131 consisting of a capacitor 131a, a resistor 131b and a diode 131c, forming a conventional differentiating circuit and providing the differentiated pulse output on line 132.

The differentiated pulse on line 132 is directed over line 133 as an asynchronous setting input to the compensation control flip-flop 127. The flip-flop 127 controls the flip-flop 105 since the Q output of the flip-flop 127 is the controlling condition on the "setting" input of the flip-flop 105, over line 134. This, in turn, controls the actual counting rate, over line 119, to the counter 107. In this regard, when the Q output of the control flip-flop 127 is "true", the flip-flop 105 is asynchronously forced into its "true" state which thereby enables the AND gate 106 to pass the full rate multiplier pulse rate (RM to the counter 107. In contrast, when the Q output of the flip-flop 127 is "false", the flip-flop 105 behaves as a divide-by-two binary counter, and only every other RM pulse from the rate multiplier 102 is passed over line 121, through gate 106, to the counter 107.

Gate 112 controls the clocking input over line 136, to the control flip-flop 127, the gate 112 having as its three inputs, the CLK signal over line 137, the Q state of the control flip-flop 127 over line 138, and the 404 Hz. fill frequency over line 111.

A direction sensor 140, forming part of the direction control subsystem for the forward-reverse and speed control logic, typically forms part of the mechanical valve control subsystem for the syringe cartridge and typically comprises a light and photocell combination which generates an electrical output indicative of whether or not the valve control subsystem is conditioned for a pump stroke or a fill stroke of the operational cycle.

The direction sensor 140 is schematically illustrated as a switch 140a which provides a "0" input when the syringe has reached the "pump" position (about to initiate a pump stroke) and provides a "1" input when the syringe has reached the "fill" position (about to initiate a fill stroke). In other words, when the syringe cartridge has completed a pump stroke, and is about to begin a fill stroke, the switch 140a closes to the "fill" position and enables the D input of a timing flip-flop 141. The flip-flop 141, together with a second timing flip-flop 142, are used to synchronize the input from the direction sensor 140 with the actual clocking of the overall system. The timing flip-flops 141, 142 are clocked by the 40.4 Hz. frequency output from the rate multiplier 102, on line 115, which provides clocking inputs to these flip-flops over lines 143, 144, respectively.

When the pump mechanism reaches the end of its stroke in either direction, the timing flip-flop 141 changes state on the first 40.4 hertz pulse which occurs on line 143. On the very next 40.4 Hz. pulse, the timing flip-flop 142, which has its D input connected to the Q output of the flip-flop 141, over line 146, follows the setting of the flip-flop 141, thus providing a pulse period delay of approximately 24.75 milliseconds during which the pair of flip-flops 141, 142 are not in the same state. The latter time interval is used to stop the stepping motor so that it has time to reverse properly, rather than calling for reverse rotation of the motor without providing adequate time for coming to a stop between strokes.

AND gates 148, 149, 151, 152 and OR gates 154, 155 comprise the gating for the speed control subsystem and receive the CLK signal over line 101, the pump frequency signal over 109 and the fill frequency signal over line 113, to selectively provide output motor drive pulses of appropriate frequency, over line 157, depending upon whether a fill stroke or a pump stroke is to be performed, as input to the stepping motor driver 158 for the syringe pump.

Having thus identified the major subsystem components in the pump rate, fill rate and motor drive pulse generating and control subsystems, the basic operation of these subsystem areas, particularly as disclosed in FIGS. 6a and 6b are next described.

As previously pointed out, the clock 100 feeds high frequency clocking pulses over line 101 to the rate multiplier 102 and the electrical output (RM) of the rate multiplier, over line 103, is a pulse frequency proportional to the clock frequency times the rate selector switch setting established by the switches 102a. For example, if the rate selector switches have been set to "100", representing a desired output pumping flow rate of 100 cc. per hour, the RM output frequency would be 100/1000 or 1/10th of the CLK frequency, which is 4.04 kilohertz. If the rate selector switches are set to "10", representing 10 cc. per hour, the RM frequency would be 10/1000 or 1/100th of the clock frequency, which is 404 Hz. The RM output frequency from the rate multiplier 102, over line 103, is the normal frequency for driving the flip-flop 105, assuming the Q output of the control flip-flop 127 is "false". In this connection, the flip-flop 105 has its $\bar{Q}$ output tied to its D input in a conventional toggle arrangement. This causes the flip-flop 105 to alternate its Q output state with each clock pulse received over line 117, thus converting the flip-flop 105 into a binary counter with the output frequency on line 121 from the Q output terminal of the flip-flop being half of the input pulse frequency to the clocking input of the flip-flop.

The same RM frequency passed by the AND gate 104, over line 117, to the clocking input of the flip-flop 105 is also directed over line 118 as one input to the AND gate 106. The other inputs to the gate 106 are the CLK signal over line 101 and the Q state of the flip-flop 105, over line 121. Hence, the gate 106 is enabled only when the Q output of the flip-flop 105 is "true". Since the flip-flop 105 is a divide-by-two binary counter, its Q output will be "true" only on every other RM pulse. Hence, the electrical output over line 119 to the counter 107 is half of the frequency of the RM input pulse train to the gate 106.

The counter 107 counts up to a state of "101" and the latter counting state is decoded out by the AND gate 108 which receives the "1", "4", "32", and "64" states of the counter flip-flops, over lines 110, as gate inputs. When the gate 108 goes "true" on the count of "101", the electrical output on line 109, together with the very next RM pulse over line 128, enables the NAND gate 125 to pass the next CLK pulse which overlaps with the RM pulse. In this regard, the electrical output of the NAND gate 125 is normally positive and goes negative when enabled, for the period of a single clock pulse. The electrical output pulse from the enabled gate 125 is differentiated by the differentiator 131 and provides a reset pulse output over line 132.

The reset output from the differentiator 131 is fed to the reset inputs of the high order decades of the rate multiplier 102, over lines 162, 163, is directed over line 133 to the "set" input of the compensation control flip-flop 127 and is also fed over line 164 to the "reset" input of the counter 107.

The reason for resetting the BCD rate multiplier 102 at the "101" state of the counter 107 is that the rate multiplier in the system of FIG. 6a is also being used to generate the fill frequency over line 111. Since the "101" counter state of the counter 107 is not necessarily synchronous with the count in the rate multiplier 102, the high order decades 102b and 102c of the rate multiplier (used to generate the fill frequency) must be reset to "zero" at the beginning of each pump stroke motor drive pulse period. This is necessary since the fill frequency output of the rate multiplier 102 is being used, through the AND gate 112, to reset the compensation control flip-flop 127, and the time period between setting and resetting of the latter flip-flop must be exactly equal to a single fill stroke motor drive pulse period, i.e., 1/404 seconds. If the high order decades 102b and 102c of the rate multiplier 102 were not reset at the "101" state of the counter 107, the time period between setting and resetting of the control flip-flop 127 would usually be shorter than the desired fill frequency pulse period and would introduce errors into the frequency compensation technique.

The "reset" pulse over line 164 forces the counter 107 to its "zero" state, and simultaneously forces the control flip-flop 127, through its "set" input over line 133, to the "true" state. With the flip-flop 127 now set so that its Q output is "true", the divide-by-two flip-flop 105 is also forced into the "true" state through its "set" input over line 134. The flip-flop 105 is thus "set" asynchronously and is therefore independent of its clocked input over line 117.

Hence, as long as the Q output of the control flip-flop 127 remains "true", the Q output of the flip-flop 105 also stays "true" and enables the AND gate 106, over line 121, continuously as long as these conditions subsist. This results in all of the RM pulses from the rate multiplier 102 being fed through the enabled gate 106, over line 119, to the counter 107. Thus, during the entire time period that the flip-flop 127 (and hence the flip-flop 105) remains "true", the counting input over line 119 to the counter 107 is at twice the pulse frequency that would otherwise occur. The counter 107 is thus counted up during this period at twice the normal rate, i.e., at the full RM pulse rate.

Counting at the full RM pulse rate continues, until the rate multiplier output over line 111 completes a single 404 Hz. pulse period (2.475 milliseconds), thus providing a "true" output on line 111 as one input to the AND gate 112, the other inputs to the gate 112 being the CLK signal on line 137 and the "true" Q output of the flip-flop 127. Hence, since all of its inputs are "true", the clock pulse passes through the AND gate 112 to the clocking input of the control flip-flop 127 and resets the flip-flop 127 so that its Q output goes "false". The reason this change of state occurs, is because the $\overline{Q}$ output of the flip-flop 127 is tied to the D input of the flip-flop, as in the case of the flip-flop 105, thus establishing the flip-flop 127 as a toggle or binary counter which alternates states each time its clocking input is pulsed.

It will be apparent that, when the compensation control flip-flop 127 goes "false", the "set" input of the flip-flop 105 is also "false", so that the flip-flop 105 resumes operation as a binary counter, whereby the RM pulse train output from the rate multiplier 102 is again divided by two before being passed through the gate 106 to the counter 107. In this way, the first portion of the counting cycle defining each pump stroke motor drive pulse period is counted up, for a time interval equal to one fill stroke motor drive pulse period, at twice the normal counting rate which prevails over the balance of the pump stroke motor drive pulse counting cycle. Hence, compensation is accomplished, as in the simplified system of FIG. 3, and as illustrated graphically in FIGS. 4 and 5 previously discussed.

FIGS. 7a through 7g are timing waveforms which further amplify the functions and operation of the frequency determination and compensation subsystems described in connection with FIG. 6a. FIG. 7a illustrates the CLK output from the clock 100 which is a regularly occurring clock pulse train, the numbers above the clock pulses representing the counting state of the rate multiplier 102 (high order decades).

It has been assumed, for purposes of illustration, that the rate selector switches 102a have been set to a flow rate of 300 cc. per hour, which means that the actual counting frequency out of the rate multiplier 102 is 0.3 times the clock frequency (CLK). Hence, it will be apparent in FIG. 7b, that the RM pulse output from the rate multiplier shows three RM pulses for each ten CLK pulses. However, since the number "10" is not exactly divisible by the number "3", the RM output pulse train is not evenly distributed in the groups of ten CLK pulses. Rather, the RM pulses come in non-uniform bunches, and for the particular way illustrated for decoding the rate multipliers, FIG. 7b shows RM output pulses on the "2", "4" and "7" counts of the rate multiplier.

FIG. 7c shows the "Q" output of the binary counter flip-flop 105 which constitutes the divide-by-two network. It will be apparent from the left half of the waveform, that the flip-flop 105 is dividing the pulse train frequency RM of the rate multiplier 102 in half, by producing a single output pulse waveform for every two RM pulses.

FIG. 7d illustrates the counting pulses directed as input to the counter 107 and further illustrates the output counting state of the counter 107. The left half of the waveform shows the upper counting states "98" through the overflow count of "101" leading up to the "reset" condition where the next RM pulse resets the counter 107 to its "zero" state. The right half of the waveform shows how, after the counter 107 has been "reset", the counter is then counted up at twice the rate.

FIG. 7e is a waveform of the electrical output of the NAND gate 125 and illustrates the nature of the NAND gate output when the gate is enabled by the coincidence of the "101" count from the counter 107 (through AND gate 108) with the RM output from the rate multiplier 102 and the CLK output from the clock 100. In this regard, the normally positive output of the NAND gate 125 goes negative. The RM output pulse which counts the counter 107 to the "101" state does not generate an output pulse from the NAND gate 125. Instead, the next RM pulse, which does not pass as counting input to the counter 107 since the Q output of the flip-flop 105 is then "false", gates the next clock pulse through the NAND gate 125 (rate multiplier counting state "4") to create a negative pulse out of the NAND gate with a period equal in duration to the positive clock pulse.

FIG. 7f illustrates the electrical output of the differentiator 131 and shows a "reset" pulse in the form of a positive spike, shorter than the normal CLK period, generated by the positive going output (trailing edge of the negative pulse) of the NAND gate 125 (FIG. 7e). As can be seen from the timing waveforms, the "reset" pulse from the differentiator 131 appears at the time that the clock goes from its "true" state to its "false" state, or from a positive to a negative transition, assuming positive logic.

FIG. 7g illustrates the Q output of the compensation control flip-flop 127 which enables counting up of the counter 107 at double the count rate (i.e., at the full RM output rate) for the period of 100 clock pulses, the latter being the period of a single motor drive pulse at the fill frequency of 404 Hz.

Considering now the transition period for the "101" count state of the counter 107, assume that the counter input has just placed the counter in the "101" state. As a result, the gate 108 has been enabled and the binary flip-flop 105 has also been "reset". It will be observed that the counting input to the counter 107 is generated by coincidence of the "true" state of the flip-flop 105 and the occurrence of an RM rate multiplier pulse. Therefore, the same pulse that advances the counter 107 to its "101" state also always resets the flip-flop 105. The very next rate multiplier pulse will now enable the NAND gate 125, but, as previously indicated, does not count up the counter 107 because of the "false" Q output from the flip-flop 105 which had been reset. At the end of the clock period, the "reset" output appears from the differentiator 131 to force the flip-flop 127 into its "true" state (FIG. 7g) while simultaneously resetting the rate multiplier to its "zero" state (FIG. 7a). From this point on, the flip-flop 127 will remain "true", which results in the flip-flop 105 being forced into the "true" state through its asynchronous "set" input. This, in turn, results in enablement of all of the RM pulses into the counter 107. All of the changes in counting state of the counter 107 occur at the same times that the RM pulses appear, with a one-to-one pulse correlation so that the RM pulse frequency is no longer divided by two prior to counting up the counter 107.

After 100 clock pulses, or a period equal to 2.475 milliseconds, at the "9" state of the rate multiplier, the fill frequency signal enables gate 112 at the clock transition from "true" to "false" and resets the flip-flop 127. The flip-flop 105, however, stays "true" for one more RM pulse. This latter RM pulse will still be passed as a counting pulse to the counter 107, but the flip-flop 105 will be "reset" at the same time and, from that point on, alternate RM pulses will be suppressed by the divide-by-two flip-flop 105.

The reason should now also be apparent for resetting the high order decades of the rate multiplier 102. Since the decoding provides the divide-by-ten output at the count of "9", the rate multipliers could start out at any number other than zero, just by chance, if the rate multipliers were not "reset" at the beginning of each counting cycle of the counter 107. Such a random state of the rate multiplier would shorten the period of time during which counting is accomplished at double counting rates for compensation purposes. This time for doubling the counting frequency could vary randomly from zero to 2.475 milliseconds, whereas correct compensation calls for double counting rate of the counter 107 for exactly 2.475 milliseconds during the generation of each pump stroke motor drive pulse.

Referring now more particularly to FIG. 6b, forward-reverse speed control, i.e., the selection of fill frequency or pump frequency for the motor drive pulses over line 157 to the stepping motor driver 158, is next described.

Directional control, as previously indicated, is accomplished with the aid of the timing flip-flops 141, 142 under the control of the direction sensor 140. When the switch 140a is closed, indicating that the valve control system is at the end of the pump stroke and prepared to initiate a fill stroke, a non-synchronous enabling signal is directed over line 170 to the D input of the flip-flop 141. The clocking input of the flip-flop 141 receives the 40.4 Hz. signal from the rate multiplier 102, over line 143, and will set the flip-flop 141 "true" on the very next 40.4 Hz. clock pulse.

The "true" state of the flip-flop 141 is directed over line 146 to the D input of the flip-flop 142 and, a single 40.4 Hz. pulse period later, i.e., 24.75 milliseconds later, the flip-flop 142 will also be set "true" on the very next 40.4 Hz. pulse, directed over line 144 to the clocking input of the flip-flop 142. Hence, the flip-flop 142 always follows the flip-flop 141 by a period of approximately 25 milliseconds, thus providing sufficient time for the stepping motor driver 158 to come to a complete stop after each stroke and reverse direction for the next stroke.

It will be apparent, therefore, that with the Q outputs of both flip-flops 141, 142 "true", the system is about to perform a fill stroke to fill the syringe cartridge from a suitable liquid source, whereas when the Q̄ outputs of both flip-flops are "true", the system is about to perform a pump stroke. When the flip-flops 141, 142 are not set to the same state, the system is in the minimum 25 millisecond transient period between strokes, allowing the motor to come to a stop and reverse.

It will also be apparent that, while the minimum period for switching both of the flip-flops 141, 142 from one state to another is approximately 25 milliseconds, the period can be as long as twice that period. The latter condition would occur if the asynchronous signal over line 170 from the direction sensor 140 occurs immediately after a 40.4 Hz. clocking input on line 143 has just occurred, thus requiring an additional 40.4 Hz. clock perod (25 milliseconds) before the first timing flip-flop 141 changes state. In contrast, if the signal over line 170 occurs immediately before such a clocking pulse on line 143, the period for motor reversal will be at the minimum time of 25 milliseconds, since the timing flip-flop 141 will change state almost immediately.

The AND gate 148 receives as inputs, over lines 172, 173, the Q outputs of both of the flip-flops 141, 142, respectively. The output of the AND gate 148, over line 175, will only be "true" when both of its inputs from the timing flip-flops 141, 142 are "true". However, since the Q states of both flip-flops 141, 142 being "true", defines the "fill" state for the system, a "true" output from the gate 148 over line 175 indicates performance of a fill stroke. The latter output over line 175 passes through the OR gate 154 as enabling input over line 176 to the AND gate 151, the other input to the gate 151 being the 404 Hz. fill frequency over line 113. The fill frequency is thus passed by the enabled gate 151, over line 178, through the OR gate 155, and over line 179 as input to the motor drive pulse AND gate 152, the other input to the gate 152 being the CLK pulse over line 101 for synchronization purposes. Hence, during the fill stroke of the syringe pump, motor drive pulses to the stepping motor driver 158 are provided on line 157 at the output of the gate 152, at the designated fill frequency of 404 Hz.

When the syringe is completely filled, the valve control subsystem conrolling the direction sensor 140 causes the switch 140a to open to the "pump" position and thereby provides a "false" input to the D terminal of the flip-flop 141. The next 40.4 Hz. clock pulse, over line 143, resets the flip-flop 141 "false" which immediately disables AND gate 148 and, consequently, also disables the fill frequency AND gate 151 (through the OR gate 154), so that no further motor drive pulses are generated at the fill frequency. Indeed, as will become apparent, in the time interval during which the timing flip-flops 141, 142 are in different states from each other, no motor drive pulses at all are provided to the stepping motor driver 158, thus allowing the motor to stop between strokes prior to reversing direction.

Another 24.75 milliseconds later, the timing flip-flop 142 follows the setting of the flip-flop 141 and goes "false", thus establishing the "pump" state where the Q̄ outputs of both flip-flops 141, 142 are "true". The Q̄ outputs of the timing flip-flops 141, 142 are both directed as enabling inputs over lines 181, 182, respectively, to the pump frequency AND gate 149 which receives as a third input over line 109 the pump frequency output from the counter decding gate 108 (FIG. 6a). A fourth input to the pump frequency gate 149, over line 183, is normally "true", except when the system is being initially started and no syringe cartridge has yet been installed.

Assuming, for the moment, that the syringe cartirdge is already installed, all inputs to the pump freqüency gate 149 are "true", thus passing the pump frequency over line 185, through OR gate 155, over line 179, through AND gate 152 in synchronism with the CLK frequency, to provide frequency compensated motor drive pulses on line 157 at the selected pump flow rate in accordance with the setting of the rate selector switches 102a (FIG. 6a).

Again, when the pump stroke has been completed, the timing flip-flop 141 will again change state, the motor will come to a stop during the transition period when the flip-flops 141, 142 are in different states (with all motor drive pulses being gated off) and, when the flip-flops 141, 142 assume the same state after the transition period, motor drive pulses of the appropriate frequency will again be directed over line 157 to the stepping motor driver 158.

The particular direction in which the stepping motor driver 158 rotates is determined by conventional forward-reverse control logic well known in the art for such stepping motors and, the control signal for such conventional circuitry is directed to the motor driver 158, over line 187, from he $\overline{Q}$ output of the timing flip-flop 142. Typically, such stepping motors involve a two-phase drive system with two separate windings. The current is alternately inverted in one of these windings at a time. Therefore, to make one step of the motor, the current is inverted in one of the windings, while the next step is accomplished by inverting the current in the other of the pair of windings. The forward or reverse rotation of the motor is dependent merely on the relative phase of the two windings.

The alarm and start-up subsystems for the syringe pump will now be more specifically decribed, reference being made particularly to FIG. 6c for the ensuing description.

The alarms subsystem contains a drop detector 190 which is essentially a combined light beam and photocell detector, as previously described in connection with the drop detector 20 in the basic system of FIG. 1.

A drop rate discriminator 191 generates an output signal if the drops sensed by the drop detector 190 are received at below a prescribed minimum rate. Since the syringe cartridge is filled during the fill stroke at a preestablished, fixed flow rate of 5 cubic centimeters in approximately 9 seconds, the minimum rate at which drops should appear in the drip chamber of the I.V. set is readily ascertainable. If the drop rate is below the prescribed minimum, the drop rate discriminator 191 generates an output signal which is used to place tha system into alarm. The drop rate discriminator 191 includes a conventional diode pump rate meter circuit well known in the art, the rate meter feeding an appropriate gate having a threshold representing the minimum drop flow rate and thereby providing the desired discrimination function.

An AND gate 193 is the alarm gate for leak detection during a pump stroke, i.e., the detection of drop flow in the drip chamber when a pump stroke is being performed, while a NOR gate 194 is the alarm gate for leak detection or detection of an exhausted liquid source during the fill stroke. A delay 195, typically a conventional resistance-capacitance delay circuit, introduces a delay of approximately two seconds in the response of the leak detection gates 193, 194 at the beginning of a pump stroke in the case of the gate 193 and at the beginning of a fill stroke in the case of the gate 194.

The reason for the introduction of the delay 195 is that, when the syringe is just beginning to be filled, there is usually no actual drop flow in the drip chamber since it takes a short period of time for the pressure to build when the fill stroke begins. Therefore, a short delay is needed during this initial "no drop" period to avoid going into an immediate false alarm condition. The same delay is also used after the fill stroke has been completed since when the motor stops, drops may still fall through the drip chamber of the I.V. set for a very brief interval. These drops, if detected at the beginning of the pump stroke, would otherwise indicate a leak in the system and, likewise, produce an immediate false alarm condition.

An air detector 197, typically comprising a light emitting diode and photocell detector combination, disposed on opposite sides of the I.V. tube or syringe cartridge nipple, detects any air bubbles passing through the line which interrupts a reference light beam and generate an output pulse for placing the system into alarm.

A "power on and reset" subsystem 198, which is essentially a delayed signal produced whenever the main power switch is turned on, provides a "true" signal for a prescribed period of time until all of the power supplies have reached their normal operating voltages and all of the required delays have occurred for the overall system electronics to initialize to its normal operating state.

The subsystem 198 is used to force the system initially into an alarm condition when the power is first turned "on" and is also used to sense the condition when the power is "on" but no syringe cartridge has yet been installed in the pumping apparatus. In this regard, a syringe detector 199, which may also be a light beam and photocell sensing arrangement to detect the physical presence of a syringe cartridge, is utilized. The detector 199 provides an output signal which is inverted by an inverter 201 and, in conjunction with other gating, forces the system to generate a control signal, when the power is first turned "on" and no syringe cartridge has been detected. This control signal (GTS) causes the syringe piston actuator (represented by the drive subsystem 12 in FIG. 1) to be driven all the way to the end of the pump stroke in preparation for subsequent initiation of a fill stroke after a syringe has been properly installed and detected.

This is another feature of the invention, in that it has been determined that a syringe should be completely empty and mounted into the pumping apparatus with the syringe piston all the way in (towards the inlet and outlet ports in FIG. 1) as the prescribed format for insertion of the syringe into the apparatus for initial start-up, i.e., it has been determined that system operation should begin with a fill stroke. Hence, the system is designed to force the pumping apparatus into the condition where the syringe cartridge can be easily inserted prior to actual operational start-up.

The detection of a stalled stepping motor also forces an alarm condition upon the system. The stalled motor alarm comprises a rotation sensor 203 directing an appropriate motor rotation signal to a counter 204 through an OR gate 205. The counter 204 counts motor drive pulses and is "reset" by the motor rotation signal. Such motor stalling has a greater probability of occurring when the pump is used with a downstream filter which may clog and induce high back pressure on the pumping system.

The rotation sensor 203 is typically a disc mounted on the stepping motor output shaft for rotation therewith, the disc having alternate transparent and opaque sectors. A photocell detects light from a reference light source passing through the disc, as it rotates, and generates the "reset" pulses to the counter 204. If the counter reaches a predetermined number of motor drive pulses without being "reset", the system is put into alarm.

An OR gate 207, which is the master alarm gate, collects all of the various alarm lines from the alarm monitoring subsystems previously described. The output of the alarm gate 207 is directed to a pair of cross-coupled NOR gates 209, 210 defining a latching circuit which latches either in the alarm state or in the normal system operation state. A "true" output from the OR gate 207 to the input of the NOR gate 210 will normally force the system into the alarm state.

A "start" switch 212 selectively grounds the input of the NOR gate 210 and forces the system into the normal operational state if all of the alarm conditions have been removed so that the output of the OR gate 207 is "false", thus enabling the system to start.

Another pair of cross-coupled NOR gates 214, 215 define a "start-up" latch for the system which, in conjunction with the power-on reset subsystem 198 and syringe detector 199, operate to provide an output "go to start" (GTS) signal which causes the system to operate the stepping motor driver at the high fill frequency rate and rapidly move the syringe piston actuator to the position for readily receiving a syringe cartridge and initiating a fill stroke. In this regard, an AND gate 216 is used to sense the condition where the syringe actuator has first arrived at the latter position, which occurs in the transient period between the end of a pump stroke and the beginning of the next fill stroke.

A second or back-up "no drop" alarm which normally does not operate, but assumes control if he normal "no drop" alarm failed to detect a lack of flow during a fill stroke, is used in the system to prevent the pumping of air into a patient which might otherwise be caused by a single system component failure.

The back-up "no drop" alarm system includes an accumulator-discriminator 218, an AND gate 219 and a latch 220. The accumulator-discriminator 218 is again a conventional diode pump circuit which contains a charging capacitor. The latter capacitor gets charged up by output pulses from the drop detector 190. At the end of the fill stroke, the accumulator charge is sensed and, if it is too low, the latch 220 is activated to shut off the stepping motor driver 158.

The back-up "no drop" alarm system is deactivated in the "go to start" mode which occurs when the power is turned "on" and no syringe cartridge has yet been installed. However, the back-up alarm system, once activated, cannot be reset by the start switch 212 (as in the case for other alarm conditions) since its activation indicates a basic system malfuction. The back-up alarm system can only be cleared by turning the instrument power "off".

An additional back-up alarm system is provided in the form of a high rate alarm which alarms and deactivates the stepping motor driver 158 in the event of component failure which induces a runaway condition. This condition is manifested by the pump running at maximum pumping rates, even though a low pumping rate has been selected by the rate selector switches 102a. The high rate alarm subsystem includes a rate comparator 222 which compares the motor drive pulses in the pump stroke with the current from a high order decade rate selection sensing subsystem 223 (FIG. 6a), to selectively energize the latch 220 whenever the motor drive pulses being generated exceed the drive pulse rate which should be generated in accordance with the selected fluid flow rate.

Essentially, the rate comparator 222 is a diode pump rate meter circuit that generates a current which is counteracted by the current generated by the weighted resistors in the rate selection sensing subsystem 223. Hence, the rate meter generates a current which is proportional to the frequency of the motor drive pulses in the pump stroke. This current is compared with the current generated by a series of weighted resistors 223a–223d connected to the high order rate selector switches 102a. Thus, when the current sensed by the rate meter exceeds the current generated by the resistors, the system is put into alarm by activation of the latch 220 which then prevents the stepping motor driver 158 from running. Again, this alarm can only be cleared by turning off the electrical power, since activation of the alarm indicates a basic system malfunction.

With the aforedescribed outline of the basic alarms and start-up subsystems components and their functional interrelationship, the various operational sequences for these subsystems are further detailed in the following description.

As previously indicated, the NOR gates 209 210 are electrically interconnected as a cross-coupled latch which essentially defines a non-synchronous set-reset alarm flip-flop providing an output over line 225 defined as the alarm signal (ALA). The ALA signal is also directed over line 226 to the stepping motor driver 158 (FIG. 6b) and thereby provides, by conventional stepping motor circuitry, a shut-off control signal for turning off the power to the stepping motor.

The NOR gate 214, 215 represent another cross-coupled latch which is the "start-up" latch for syringe cartridge loading, and the latter latch gets activated when the system power is first turned "on" and a syringe cartridge has not yet been installed. In this regard, regardless of the position of the syringe piston actuator in the drive system, when the power is first turned "on", it will always be driven to its position at the completion of a pump stroke, so that the syringe cartridge can be easily inserted in preparation for a fill stroke.

Assume, for purposes of explanation, that a syringe has not yet been installed, and the syringe piston actuator of the drive system is in some random position between initiation and completion of any stroke. When the electrical power is initially turned "on", the power on reset subsystem 198 provides for a brief period, typically 200 milliseconds, a "true" output signal over line 228 which is also directed over line 229 as an input to the alarm gate 207, consequently providing a "true" output from the latter gate, over line 230, as an input to the NOR gate 210. This drives the output of NOR gate 210, over line 231, "false". The power on reset signal on line 228 is also directed as an input to the NOR gate 214, thus driving the output of that gate likewise "false" on line 233.

Since a syringe has not yet been installed, the syringe detector 199 provides a "false" output, over line 234, as one input to the NOR gate 215. The gate 215 receives a second "false" input, over line 235, from the output of the NOR gate 214 previously discussed. The gate 215 receives a third input, over line 236, from the gate 216 which is normally disabled and therefore provides a normally "false" output. Hence, since all of its inputs are "false", the NOR gate 215 is enabled and provides a "true" output on line 237 which is defined as the "go to start" (GTS) signal.

The "true" output (GTS) of the gate 215 is also directed as an input, over line 238, to the NOR gate 214. The latter input holds the gate 214 disabled to maintain a "false" output, over line 235, as input to the gate 215

(even after the power on reset period has passed), and therefore latches the NOR gate 215 in the "true" (GTS) state.

The "true" output of the gate 215, or GTS signal, is also directed over lines 240, 241 as one input to the NOR gate 209, thus holding the output of the gate 209 "false". Although the power on reset subsystem 198, through the alarm gate 207, has activated one input of the NOR gate 210 on line 230 and, therefore, resulted in a "false" input to the gate 209 over line 231, the "true" GTS signal on line 241 still holds the output of the gate 209 "false" and therefore prevents the system from going into alarm and shutting off the stepping motor driver 158. Moreover, as soon as the power on reset period has passed, both of the inputs to the NOR gate 210 will be "false", since the "false" output of the gate 209 is connected over line 243 as the second input to the gate 210, thus driving the output of the gate 210 "true" on line 231, to again latch the gate 209 so that its ALA signal output is held "false". This defines the stable "go to start" or GTS condition.

The electrical output of the NOR gate 215, or GTS signal, is directed over line 240 as an input to the OR gate 154 (FIG. 6b) which enables the AND gate 151, over line 176, to pass the 404 Hz. fill frequency through gates 151, 155 and 152 and thereby provide fill frequency motor drive pulses over line 157 to the stepping motor driver 158. Hence, the gate 151 is enabled by the GTS signal independently of the gate 148 and, therefore, independent of the status of the direction control timing flip-flops 141, 142.

The fill frequency drive pulses energize the stepping motor driver 158 until the system senses that the syringe piston actuator has been driven to the position which indicates completion of a pump stroke and transition to a fill stroke, the latter condition signaling the end of the "go to start" or GTS state. The GTS signal over line 240 is also directed through an inverter 242 (FIG. 6b) to disable the AND gate 149 and thereby prevent the pump frequency from being applied simultaneously with the fill frequency while the system is in the GTS state with no syringe cartridge yet installed.

It is, of course, necessary to disable the stepping motor driver 158 when, at the end of the GTS state, the desired position of the syringe piston actuator has been reached, so that a syringe cartridge can be installed. In this regard, as the piston actuator is moving towards the desired position calling for initiation of a fill stroke, the system will be performing a pump stroke, which means that the $\overline{Q}$ output of the timing flip-flop 142 will be "true".

As soon as the pump stroke has been completed, the direction sensor 140 will be switched to the "fill" position and the timing flip-flop 141 will be set "true" while the flip-flop 142 remains "false" for a period of 24.75 milliseconds. It will be apparent that, when the flip-flop 142 is "false", its $\overline{Q}$ output over line 244 provides a "true" input over line 245 to the AND gate 216. In addition, while the flip-flop 141 is "true", the other input to the AND gate 216, over line 246, is likewise "true", thus enabling the gate 216 and providing a "true" output over line 236, as one input to the NOR gate 215. This causes the output of the gate 215 to go "false", thereby terminating the GTS signal and the "go to start" state, the latter state being latched out by the interaction of the NOR gates 215 and 214. In this regard, since no syringe cartridge has yet been installed, a "false" input over line 234 is fed to the NOR gate 215, but is of no effect in view of the "true" input over line 236 from the gate 216.

The "false" output from the gate 215, over line 238, is directed as one input to the NOR gate 214, the other input to the gate 214, over line 228, being also "false" since the power on reset period has long since passed during the GTS state. This results in enablement of the NOR gate 214 and a "true" output, over line 235, as input to the NOR gate 215 to latch the gate 215 in its "false" output state, thus holding off the GTS signal.

The absence of a syringe cartridge produces a "false" output from the syringe detector 199, the output being inverted by a "true" signal by the inverter 201 and directed over line 250 as input to the alarm OR gate 207 which results in a "true" output from the gate 207 as input over line 230 to the NOR gate 210, thus driving the output of the gate 210 "false". Since the GTS signal is now "false" as just described, both of the inputs to the NOR gate 209 are now "false", thereby enabling the gate 209 and providing a "true" output over line 225 which places the system into the alarm state and shuts off the stepping motor driver 158, via the ALA signal over line 226.

The pair of NOR gates 209, 210 are latched in this alarm condition and cannot be brought out of this condition until a syringe cartridge has been inserted and detected by the syringe detector 199, to drive the input over line 250 to the alarm gate 207 "false". When this has occurred, the "start" switch 212 is manually closed and forces the input to the NOR gate 210, over line 243, "false". In this regard, the output of the gate 209 is connected to ground by the "start" switch 212. A current limiting, series resistor 251 is provided, in view of the high level output from the gate 209. Since all of the other alarm lines providing input to the alarm gate 207 should also be "false", the other input to the NOR gate 210, over line 230, should also be "false", which makes the output of gate 210 go "true", thereby forcing the output of NOR gate 209 "false" and removing the alarm condition.

Hence, the normal "start-up" sequence of events in operating the overall syringe pump system is summarized as follows. Turning on the power with no syringe cartridge yet installed results in the "go to start" state generating a "true" GTS signal which causes the syringe piston actuator to be driven rapidly at the fill frequency to the position where a fill stroke is about to be initiated, which is the proper position for receipt of the syringe cartridge. During the transition period between the completion of the pump stroke and initiation of the fill stroke, the gate 216 disables the GTS signal and the gate 209 generates the ALA signal which shuts off the stepping motor. A syringe cartridge is then inserted and detected. Closing the "start" switch 212, after the syringe cartridge has thus been installed, latches out the alarm condition and enables normal system operation to proceed, with filling of the syringe preparatory to a pump stroke and subsequent repetitive operational cycles in the normal mode of sequential fill and pump strokes.

The drop detector 190 provides a "true" output signal over line 253 each time a drop is detected, to provide a pulse input to the AND gate 193. The gate 193 also receives input over line 254 from the $\overline{Q}$ output of the timing flip-flop 142, and thus receives a "true" enabling input whenever the system is in the pump stroke. In addition, the AND gate 193 receives a third input, over line 255, which is the pump stroke signal on line 254 delayed by the delay network 195, and which typically introduces a delay of approximately two seconds. Hence, after the delay has passed, the input over line 255 to the gate 193 will be "true" only while a pump stroke is being performed. Therefore, if any drops are detected by the drop detector 190 after this delay period, the output of the gate 193 will go "true", over line 257, as an input to the alarm gate 207, putting the NOR gates 209, 210 into the alarm condition. In this regard, no drops should be detected during the normal pump stroke. The purpose of the delay 195, as previously indicated, is to avoid going into a false alarm condition, since drops may continue just momentarily at the beginning of the pump stroke.

When the system is performing a fill stroke, the $\overline{Q}$ output of the timing flip-flop 142 will be "false", disabling gate 193 so that the latter gate cannot possibly place the system into an alarm condition. However, the "false" $\overline{Q}$ output of the flip-flop 142 provides an enabling input, over line 254, to the NOR gate 194 which can go "true" only when all of its inputs are "false". Another input to the NOR gate 194, over line 255, is the delayed $\overline{Q}$ output signal from the flip-flop 142, which will go "false" only after approximately two seconds. The third input to the NOR gate 194, over line 259, is the output of the drop rate discriminator 191.

In the fill stroke, a prescribed minimum drop rate should appear in the drip chamber of the I.V. administration set and be detected by the drop rate discriminator 191. If the detected drop rate is below the prescribed minimum rate, the output of the discriminator 191 goes "false". The latter condition, in turn, provides a third "false" input to the NOR gate 194, thus enabling the gate 194 to provide a "true" output, over line 260, as input to the alarm gate 207 which places the system into an alarm state through the cross-coupled NOR gates 209, 210. If, however, the detected drop rate is above the prescribed minimum rate, then the output of the discriminator 191 will be "true", and the output of the NOR gate 194 will be "false", thus avoiding the alarm state.

The operation of the aforedescribed "no drop" leakage detection subsystems is further described in connection with the waveforms of FIGS. 8a–8d.

FIG. 8a indicates the $\overline{Q}$ output status of the direction control timing flip-flop 142 (FIG. 6b) and indicates that when $\overline{Q}$ is "true", the system is in a pump stroke, whereas, when $\overline{Q}$ is "false", the system is in a fill stroke.

FIG. 8b illustrates the electrical output of the delay 195, over line 255, to the AND gate 193 and NOR gate 194. Note that the resistance-capacitance circuitry of the delay 195 builds up voltage whenever the $\overline{Q}$ output of the flip-flop 142 is "true", and decays through a similar delay period when the $\overline{Q}$ output goes "false".

Referring now to FIGS. 8c and 8d, the waveforms depict the effects of the combination of enabling inputs on the AND gate 193 in FIG. 8c, and on the NOR gate 194 in FIG. 8d. The combined gate inputs are from the $\overline{Q}$ output of the timing flip-flop 142, over line 254, and the delayed $\overline{Q}$ output signal from the delay 195, over line 255. In FIG. 8c, the combined inputs to the AND gate 193 are enabling when the signal is high, and the inputs are disabling when the input is low. In FIG. 8d, the combined inputs to the NOR gate 194 are enabling when the signal is low and the inputs are disabling when the signal is high.

In FIG. 8c, it will be apparent that the input to the gate 193 is enabled with a delay from the time that the system switches from the "fill" state to the "pump" state. However, the gate is disabled immediately in switching from the "pump" state to the "fill" state. Hence, the gate 193 will not place the system into alarm, even though some drops may be detected during the initial portion of the pump stroke, so long as no drops are detected after the delay period has been completed and the gate 193 is enabled to respond to such detected drops.

In contrast, as observed in FIG. 8d, the input circuitry of the NOR gate 194 is enabled during the fill stroke and is disabled immediately when the system switches from the fill stroke to the pump stroke. However, the NOR gate 194 input circuitry is not enabled again until after the delay period has passed in switching from the pump state to the fill state. Hence, the gate 194 will not generate a false alarm at the beginning of the fill stroke, even though no drops have yet been detected, so long as the drop rate has built up to the prescribed minimum level by the time that the delay has passed and the gate 194 is enabled.

The bubble detector alarm includes the air detector 197 which, as previously indicated, typically comprises a photocell and reference light beam combination across some portion of the transparent I.V. line or across one nipple of the syringe cartridge. If the air detector senses bubbles, which are detected by interruption of the light beam, a "true" signal is produced by the air detector, over line 262, to the alarm gate 207 which places the system into an alarm condition and shuts off the stepping motor driver 158.

The back-up "no drop" alarm subsystem, comprising the drop detector 190, accumulator-discriminator 218, AND gate 219 and latch 220 senses if a sufficient number of drops were received during the fill stroke. If a sufficient number of drops were not received, and the primary "no drop" alarm system has not been enabled for some reason, as might occur in the case of a faulty system component, the back-up system will turn off the system power to the stepping motor driver 158. The back-up "no drop" alarm subsystem is effective only subsequent to the operation of the normal leakage detection subsystem. In this regard, the normal "no drop" alarm system will be activated during the fill stroke, in the manner previously described, whereas the back-up system will be activated only after the fill stroke has been completed.

The accumulator-discriminator 218 is also a diode pump circuit similar to the circuitry used for the drop rate discriminator 191, and the latch 220 is typically an operational amplifier but could readily be other circuitry such as a set-reset flip-flop or a pair of cross-coupled NOR gates similar to the gates 209, 210. When the latch 220 is activated, it provides an electrical output, over line 264, to shut off the stepping motor driver 158.

The electrical output of the accumulator-discriminator 218, over line 265, is normally "true", and is directed as one input to the AND gate 219. The gate 219 also receives an input, over line 266, which is the Q state of the timing flip-flop 142, and receives an additional input over line 267 from the $\overline{Q}$ output of the timing flip-flop 141. Both of these inputs over lines 266, 267 will be "true" at the very end of a fill stroke when the flip-flop 141 has just been set "false" to indicate that a pump stroke is next to be performed. An additional input to the gate 219 is provided, over line 268, from the output of the NOR gate 214, the latter input only being "true"

when the system is not in the "go to start" state, during which time the alarms should be deactivated.

The Q state of the timing flip-flop 142 is also directed, over line 266, to the accumulator-discriminator 218 so that the discriminator is operative only during the fill stroke. The accumulator-discriminator 218 receives an input, over line 269, from the drop detector 190 and goes "false" when the correct number of drops have been detected. Hence, when the system switches from the fill stroke to the pump stroke, the gate 219 will stay disabled if enough drops have been detected to provide a "false" output from the accumulator-discriminator 218 over line 265. On the other hand, if a sufficient number of drops were not detected by the drop detector 190 during the fill stroke, the output of the accumulator-discriminator 218 over line 265 will be "true", the AND gate 219 will be enabled during the transition from the fill stroke to the pump stroke, and an output will be directed over line 270 to set the latch 220 and shut off the stepping motor driver 158.

Reference is now made to the stalled motor alarm, which includes the rotation sensor 203, the OR gate 205 and the counter 204. The counter 204 is continuously reset over line 272 each time a pulse is generated by the rotation sensor 203, over line 273, through the OR gate 205. The counter 204 is counted up, over line 274, by the stepping motor drive pulses from the output of gate 152 (FIG. 6b). An additional input, over line 275, is fed to the OR gate 205 from the output of the NOR gate 209. The purpose of this additional input over line 275 is to reset the counter 204 whenever there is an alarm state, so that the counter will start out in the "zero" state each time the power is turned "on". Otherwise, the counter might come on in any random state and the next motor drive pulse could put the system into alarm. In this connection, unless the system is in the "go to start" state, the system alarms whenever the power on reset subsystem 198 is activated, as previously indicated. However, when the "start" switch 212 is closed after installation of a syringe, and the power on reset period has passed, the ALA signal is latched out.

The high rate alarm subsystem, comprising the rate comparator 222, the high rate selection sensing subsystem 223 (FIG. 6a), an AND gate 277 and the latch 220 is next described.

The rate comparator 222 is typically a diode pump circuit which compares the pulse rate received over line 278 with the current generated on line 279 by the weighted resistors 223a, 223b, 223c, 223d proportional to the setting of the high order rate selector switches 102a. The pulse input, over line 278, is the output from the AND gate 277, which is only enabled by the "true" Q output of the timing flip-flop 142 (FIG. 6b) over line 244, indicating that the system is performing a pump stroke. The gate 277 receives as a second input, over line 274, the stepping motor drive pulse output from the AND gate 152 (FIG. 6b). Hence, the rate comparator 222 is operative only during the pump stroke to compare the actual motor drive pulses being generated with the flow rate actually selected by the rate selector switches 102a.

If the motor drive pulse rate is higher than the rate that has been selected, as indicated by the high rate selection sensing subsystem 223, the comparator 222 will generate a signal, over line 280 to set the latch 220 and shut off the motor drive via the latch output on line 264. The latter alarm state will only occur if a high rate of motor drive pulses is generated while the rate selector switch setting calls for a low rate of motor drive pulses. In the event a high flow rate has been called for by the setting of the rate selector switches 102a, the detection of high rate motor drive pulses will not cause the rate comparator 222 to activate the latch 220. Hence, the high rate alarm subsystem prevents an extreme runaway pumping condition which might occur, for example, if a faulty gate were to apply the fill frequency continuously to the stepping motor driver 158 and override the actual pump frequency being generated.

The aforedescribed fluid flow control system has been set forth in sufficient detail to readily enable practice of the teachings of the present invention.

The new and improved fluid flow control system of the present invention is extremely accurate, reliable and easy to use. The system provides enhanced precision in selecting and maintaining fluid flow rates over a wide range, and the system is quick to inform medical personnel of any conditions which might pose a hazard to the patient. Hence, the system of the present invention minimizes the time consuming and error prone aspects of human monitoring and flow rate adjustment and provides substantial improvement in economy, reliability, stability and accuracy over previous automatic control systems, including peristaltic pumps, syringe pumps and drop flow controllers.

It will be apparent from the foregoing that, while particular forms of the invention have been illustrated and described, various modifications can be made without departing from the spirit and scope of the invention. Accordingly, it is not intended that the invention be limited except as by the appended claims.

I claim:

1. In a system for parenteral administration of liquids at desired flow rates through a feeding tube from a liquid source to a patient, the combination comprising:
   syringe means for performing alternate fill and pump strokes to control the flow of liquid through the feeding tube;
   motor means for driving said syringe means;
   electrical pulsing means for providing output pulses to said motor means at a fill frequency and at a pump frequency to operate said syringe means; and
   digital means for automatically varying said pump frequency output pulses as a function of said fill frequency output pulses to achieve the desired flow rate.

2. A combination as set forth in claim 1, wherein said digital means compensates each of the pump frequency output pulse periods during a time interval equal to a fill frequency output pulse period.

3. Apparatus as set forth in claim 1, and further comprising:
   detection means responsive to lack of motor rotation within a defined period.

4. Apparatus as set forth in claim 3, and further comprising:
   alarm means responsive to said detection means for de-energizing said motor means.

5. Apparatus as set forth in claim 1, and further comprising:
   detection means responsive to lack of motor rotation within a prescribed number of said output pulses.

6. Apparatus as set forth in claim 5, and further comprising:
   alarm means responsive to said detection means for de-energizing said motor means.

7. In a system for parenteral administration of liquids via a syringe pump, apparatus comprising:
motor means for driving a syringe through successive fill and pump strokes during which the syringe is first filled with liquid and the liquid is subsequently delivered from the syringe;
electrical pulsing means for providing output pulses at a fill frequency and at a pump frequency to operate said motor means in said fill stroke and said pump stroke, respectively; and
electrical control means for automatically varying the pump frequency of said output pulses during said pump stroke, to compensate for time lost during said fill stroke and to achieve the desired flow rate.

8. Apparatus as set forth in claim 7, wherein said electrical control means compensates each of the pump frequency output pulse periods during a time interval equal to a fill frequency output pulse period.

9. Apparatus as set forth in claim 7, wherein said electrical control means spreads the compensation for time lost during said fill stroke uniformly over said pump stroke.

10. Apparatus as set forth in claim 7, wherein said control means includes at least one counter for determining the period between successive pump frequency output pulses.

11. Apparatus as set forth in claim 7, wherein said control means includes a pair of digital counters, one of said counters being a divide-by-two counter, said counters together determining the duration of each pump frequency output pulse.

12. Apparatus as set forth in claim 11, wherein said divide-by-two counter normally controls the counting rate into the other of said pairs of counters.

13. Apparatus as set forth in claim 12, and further comprising: means for automatically bypassing said divide-by-two counter during generation of each pump frequency output pulse period for a time interval equal to the period between successive fill stroke output pulses.

14. Apparatus as set forth in claim 7, and further including:
a syringe actuator driven by said motor means;
means for detecting the physical presence of a syringe;
means responsive to lack of detection of a syringe for energizing said motor means via said pulsing means to drive said actuator; and
means for sensing a prescribed position of said actuator for de-energizing said motor means, whereby said actuator comes to rest in a position designated as proper for syringe installation.

15. Apparatus as set forth in claim 14, wherein said motor means is a d.c. stepping motor, and said stepping motor is energized by said pulsing means at said fill frequency in response to lack of detection of a syringe.

16. Apparatus as set forth in claim 7, and further comprising:
an intake line through which the syringe is filled with liquid; and
means responsive to lack of liquid flow in said intake line during a fill stroke for generating an alarm state.

17. Apparatus as set forth in claim 7, and further comprising:
means responsive to liquid flow below a prescribed minimum flow rate during a fill stroke for generating an alarm state.

18. Apparatus as set forth in claim 17, and further comprising:
means for delaying the response to said liquid flow below a prescribed minimum flow rate, for a prescribed period of time at the beginning of each fill stroke.

19. Apparatus as set forth in claim 7, and further comprising:
an intake line through which the syringe is filled wtih liquid; and
means responsive to liquid flow in said intake line during a pump stroke for generating an alarm state.

20. Apparatus as set forth in claim 19, and further comprising:
means for delaying the response to said liquid flow, for a prescribed period of time at the beginning of each pump stroke.

21. Apparatus as set forth in claim 7, and further comprising:
alarm means responsive to lack of rotation of said motor means.

22. Apparatus as set forth in claim 21, wherein said alarm means is responsive to lack of rotation within a prescribed number of said output pulses.

23. Apparatus as set forth in claim 7, and further comprising:
means for detecting drop flow; and
means responsive, only at the end of a fill stroke, to a lack of a prescribed number of accumulated drops detected during said fill stroke for generating an alarm state.

24. Apparatus as set forth in claim 7, and further comprising:
means responsive to a high rate of output pulses in excess of those required to achieve said desired flow rate for generating an alarm state.

25. Apparatus as set forth in claim 7, and further comprising:
means for detecting the physical presence of a syringe; and
means for preventing energization of said motor means at other than said fill frequency when no syringe is detected.

26. Apparatus as set forth in claim 7, wherein said control means includes:
counting means for counting up at a normal rate the period between successive pump stroke output pulses; and
means for counting up said period between successive pump stroke output pulses at twice said normal counting rate, for a time interval equal to the period between successive fill stroke output pulses.

27. In a syringe pump including a syringe, apparatus comprising:
driving means for driving the syringe through a fill stroke in which the syringe is filled with fluid through an intake line and through a pump stroke during which fluid is delivered from the syringe through an output line;
detection means responsive to fluid flow below a prescribed drop flow rate through the intake line during said fill stroke; and
means for delaying the response to said prescribed drop flow rate for a pre-established period of time at the beginning of each fill stroke.

28. Apparatus as set forth in claim 27, and further comprising:
alarm means responsive to said detection means for de-energizing said driving means.

29. In a syringe pump including a syringe, apparatus comprising:
driving means for driving the syringe through a fill stroke in which the syringe is filled with fluid through an intake line and through a pump stroke during which fluid is delivered from the syringe through an output line; and
detection means responsive to detection of fluid flow in said intake line during a pump stroke.

30. Apparatus as set forth in claim 29, and further comprising:
alarm means responsive to said detection means for de-energizing said driving means.

31. Apparatus as set forth in claim 29, and further comprising:
means for delaying the response to detection of fluid flow for a prescribed period of time at the beginning of each pump stroke.

32. Apparatus as set forth in claim 31, and further comprising:
alarm means responsive to said detection means for de-energizing said driving means.

33. In a syringe pump, apparatus comprising:
motor means for driving the syringe through a fill stroke in which the syringe is filled with fluid through an input line and through a pump stroke during which fluid is delivered from the syringe through an output line; and
detection means responsive to lack of a prescribed number of accumulated drops detected in said input line at the end of a fill stroke.

34. Apparatus as set forth in claim 33, and further comprising:
alarm means responsive to said detection means for de-energizing said driving means.

35. Apparatus as set forth in claim 34, and further comprising:
means for disabling said detection means in the absence of a syringe.

36. In a syringe pump for delivering fluid at selected flow rates, apparatus comprising:
motor means for driving the syringe through a fill stroke in which the syringe is filled with fluid through an input line and through a pump stroke during which fluid is delivered from the syringe through an output line;
means for generating motor drive pulses to energize said motor means; and
detection means responsive to a high rate of said motor drive pulses in the absence of concurrent high flow rate selected.

37. Apparatus as set forth in claim 36, and further comprising:
alarm means responsive to said detection means for de-energizing said driving means.

38. In a syringe pump including a syringe, apparatus comprising:
means for driving the syringe through a fill stroke in which the syringe is filled with fluid through an intake line and through a pump stroke during which fluid is delivered from the syringe through an output line; and
detection means responsive to fluid flow below a prescribed drop flow rate through the intake line during said fill stroke.

39. Apparatus as set forth in claim 38, and further comprising:
alarm means responsive to said detection means for de-energizing said driving means.

40. In a syringe pump including a syringe, apparatus comprising:
means for driving the syringe through a fill stroke in which the syringe is filled with fluid through an intake line and through a pump stroke during which fluid is delivered from the syringe through an output line;
drop detection means responsive to drop flow in the intake line; and
drop rate discriminator means, responsive to said drop detection means, for sensing fluid flow below a prescribed drop flow rate through the intake line during said fill stroke.

41. In a syringe pump including a syringe, apparatus comprising:
stepping motor means for driving the syringe through a fill stroke in which the syringe is filled with fluid through an input line and through a pump stroke during which fluid is delivered from the syringe through an output line at a selected fluid flow rate;
means for generating motor drive pulses to energize said motor means; and
compensation means for compensating all of said motor drive pulses during said pump stroke for the total time lost during performance of said fill stroke.

42. Apparatus as set forth in claim 41, wherein said compensation means includes:
counting means for counting up the period between successive pump stroke motor drive pulses; and
means for counting up said period between successive pump stroke motor drive pulses, at twice the rate normally called for by the selected fluid flow rate, for a time interval equal to the period between successive fill stroke motor drive pulses.

43. in a syringe pump, the combination comprising:
a syringe actuator;
a stepping motor for driving said actuator;
means for detecting the presence of a syringe;
means responsive to the lack of presence of a syringe for energizing said stepping motor at a prescribed rate to drive said actuator; and
means for sensing a predetermined position of said actuator for de-energizing said stepping motor, whereby a syringe may be installed.

44. In a fluid pumping system for driving a disposable syringe having inlet and outlet ports and a piston slidably received within said syringe, the combination comprising:
means for selecting a desired output fluid flow rate from said syringe;
drive means for reciprocating said syringe piston, said drive means including a d.c. stepping motor;
means for generating motor drive pulses during a fill stroke;
means for generating motor drive pulses during a pump stroke; and
means for compensating the frequency of all of the motor drive pulses during said pump stroke for time lost during said fill stroke.

45. In a syringe pump, apparatus comprising:

motor means for driving the syringe through a fill stroke in which the syringe is filled with fluid through an input line and through a pump stroke during which fluid is delivered from the syringe through an output line;

rate multiplier means;

means for deriving from said rate multiplier means a pump frequency proportional to desired fluid flow rate; and means for deriving a fixed fill frequency from said rate multiplier means, said fill frequency being in excess of the maximum value of said pump frequency.

46. Apparatus as set forth in claim 45, and further including:

means for resetting the high order rate multiplier decades at the end of each motor drive pulse in the pump stroke.

47. In a fluid pumping system for driving a syringe having inlet and outlet ports and a piston slidably received within said syringe, the combination comprising:

means for selecting a desired output fluid flow rate from said syringe;

drive means for reciprocating said syringe piston through a fill stroke, in which said syringe is filled with fluid through an input line and said inlet port, and through a pump stroke during which fluid is delivered through said outlet port and an output line, said drive means including a d.c. stepping motor;

means for generating motor drive pulses during a fill stroke;

means for generating motor drive pulses during a pump stroke;

counting means for determining the duration of the period between successive pump stroke motor drive pulses; and means for counting up said period between successive pump stroke motor drive pulses, at twice the rate called for by the selected fluid flow rate, for a time interval equal to the period between successive fill stroke motor drive pulses, whereby the frequency of the motor drive pulses during said pump stroke is uniformly compensated for time lost during said fill stroke.

48. Apparatus as set forth in claim 47, and further comprising:

means responsive to detection of gas bubbles in said input line for generating an alarm state.

49. Apparatus as set forth in claim 47, wherein said drive means includes:

a syringe actuator driven by said stepping motor;

means for detecting the physical presence of said syringe;

means responsive to lack of detection of said syringe for energizing said motor to drive said actuator; and means for sensing a prescribed position of said actuator for de-energizing said stepping motor, whereby said actuator comes to rest in a position designated as proper for syringe installation.

50. Apparatus as set forth in claim 47, and further comprising:

means responsive to lack of liquid flow in said input line during a fill stroke for generating an alarm state.

51. Apparatus as set forth in claim 47, and further comprising:

means responsive to liquid flow below a prescribed minimum flow rate during a fill stroke for generating an alarm state.

52. Apparatus as set forth in claim 51, and further comprising:

means for delaying the response to said liquid flow below a prescribed minimum flow rate, for a prescribed period of time at the beginning of each fill stroke.

53. Apparatus as set forth in claim 47, and further comprising:

means responsive to liquid flow in said input line during a pump stroke for generating an alarm state.

54. Apparatus as set forth in claim 53, and further comprising:

means for delaying the response to said liquid flow, for a prescribed period of time at the beginning of each pump stroke.

55. Apparatus as set forth in claim 47, and further comprising:

alarm means responsive to lack of rotation of said stepping motor.

56. Apparatus as set forth in claim 55, wherein said alarm means is responsive to lack of rotation within a prescribed number of said motor drive pulses.

57. Apparatus as set forth in claim 47, and further comprising:

means for detecting drop flow; and alarm means responsive, only at the end of a fill stroke, to a lack of a prescribed number of accumulated drops detected during said fill stroke.

58. Apparatus as set forth in claim 47, and further comprising:

alarm means responsive to a high rate of motor drive pulses during said pump stroke in excess of those required to achieve said desired fluid flow rate.

59. In a fluid pumping system for driving a disposable syringe having inlet and outlet ports and a piston slidably received within said syringe, the combination comprising:

rate multiplier means having a plurality of rate multiplier decades;

variable rate selector switch means connected to said rate multiplier means for establishing a desired output fluid flow rate pump frequency from said rate multiplier means proportional to desired fluid flow rate from said syringe during a pump stroke in which fluid is delivered from said syringe through said outlet port and an outlet line;

means for deriving a fixed fill frequency from said rate multiplier means proportional to a specified flow rate during a fill stroke in which said syringe is filled with fluid through said inlet port and an input line, said fill frequency being in excess of the maximum pump frequency;

means for generating motor drive pulses at said fixed fill frequency during a fill stroke;

means for generating motor drive pulses at a pump frequency during a pump stroke;

counting means for counting up the period between successive pump stroke motor drive pulses;

means for counting up said period between successive pump stroke motor drive pulses, at twice the normal rate called for by the selected fluid flow rate during the pump stroke, for a time interval equal to the period between successive fill stroke motor drive pulses, whereby the frequency of the motor drive pulses to said d.c. stepping motor is compensated during said pump stroke for time lost during said fill stroke; and means responsive to said counting means for resetting the high order rate multiplier decades at the beginning of each motor drive pulse period in the pump stroke.

* * * * *

UNITED STATES PATENT AND TRADEMARK OFFICE
CERTIFICATE OF CORRECTION

PATENT NO. : 4,137,913
DATED : February 6, 1979
INVENTOR(S) : Heinz W. Georgi

It is certified that error appears in the above-identified patent and that said Letters Patent are hereby corrected as shown below:

Column 2, line 9, delete "peditric" and insert therefor --pediatric--.

Column 5, line 5, delete "Morover" and insert therefor --Moreover--.

Column 6, line 6, delete "catridge" and insert therefor --cartridge--.

Column 9, line 2, delete "drip" and insert therefor --drop--;
line 8, delete "catridge" and insert therefor --cartridge--;
line 53, after "counting" insert --cycle--.

Column 10, line 36, delete "drive" and insert therefor --drove--

Column 11, line 2, after "valve" insert --control--;
line 4, delete "recieved" and insert therefor --received--.

Column 16, line 50, close parentheses after "107".

Column 22, line 5, delete "perod" and insert therefor --period--;
line 55, delete "decding" and insert therefor --decoding--.

UNITED STATES PATENT AND TRADEMARK OFFICE
CERTIFICATE OF CORRECTION

PATENT NO. : 4,137,913
DATED : February 6, 1979
INVENTOR(S) : Heinz W. Georgi

It is certified that error appears in the above–identified patent and that said Letters Patent are hereby corrected as shown below:

Column 23, line 42, delete "tha" and insert therefor --the--.

Column 26, line 20, after "209" insert --,--.

Column 27, line 8, delete "has" and insert therefor --had--.

Signed and Sealed this

Thirtieth Day of October 1979

[SEAL]

Attest:

RUTH C. MASON
Attesting Officer

LUTRELLE F. PARKER
Acting Commissioner of Patents and Trademarks